(12) United States Patent
Katnani et al.

(10) Patent No.: US 10,335,590 B2
(45) Date of Patent: Jul. 2, 2019

(54) MRI COMPATIBLE LEADS FOR A DEEP BRAIN STIMULATION SYSTEM

(71) Applicants: Husam Katnani, Boston, MA (US); Giorgio Bonmassar, Boston, MA (US)

(72) Inventors: Husam Katnani, Boston, MA (US); Giorgio Bonmassar, Boston, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 14/850,229

(22) Filed: Sep. 10, 2015

(65) Prior Publication Data

US 2016/0331960 A1 Nov. 17, 2016

Related U.S. Application Data

(60) Provisional application No. 62/048,534, filed on Sep. 10, 2014, provisional application No. 62/132,671, filed on Mar. 13, 2015.

(51) Int. Cl.
*A61N 1/05* (2006.01)
*A61N 1/08* (2006.01)
*A61N 1/37* (2006.01)

(52) U.S. Cl.
CPC ............ *A61N 1/08* (2013.01); *A61N 1/0534* (2013.01); *A61N 1/086* (2017.08); *A61N 1/0551* (2013.01); *A61N 1/0563* (2013.01); *A61N 1/3718* (2013.01)

(58) Field of Classification Search
CPC ............ A61N 2001/086; A61N 1/3718; A61N 1/0534; A61N 1/08; A61N 1/086
See application file for complete search history.

(56) References Cited

U.S. PATENT DOCUMENTS

| 2010/0234929 | A1* | 9/2010 | Scheuermann | A61N 1/056 607/116 |
| 2013/0282090 | A1* | 10/2013 | Decre | A61N 1/0551 607/116 |
| 2014/0249612 | A1 | 9/2014 | Bonmassar et al. | |

OTHER PUBLICATIONS

Adair, et al., Thermoregulatory Responses to RF Energy Absorption, Bioelectromagnetics Supplement, 2003, 6:S17- 538.
Angelone, et al., Metallic Electrodes and Leads in Simultaneous EEG-MRI: Specific Absorption Rate (SAR) Simulation Studies, Bioelectromagnetics, 2004, 25:285-295.
Angelone, et al., Analysis of the Role of Lead Resistivity in Specific Absorption Rate for Deep Brain Stimulator Leads at 3T MRI, IEEE Trans. Med. Imaging, 2010, 29(4):1029-1038.
(Continued)

*Primary Examiner* — George R Evanisko
(74) *Attorney, Agent, or Firm* — Quarles & Brady LLP

(57) ABSTRACT

A lead for an implanted medical device is disclosed in which the lead is adapted for electrical communication with an electrical signal source and has a distal tip with an electrode. The lead comprises a wire adapted to be placed in electrical communication with electrode. The wire includes: (i) a core comprising a polymeric material, and (ii) a metallic layer surrounding an outer surface of the core. The metallic layer includes a first section having a first thickness and a second section having a second thickness, wherein the first thickness is greater than the second thickness. The lead is substantially transparent to radio frequency waves in clinically-applicable magnetic resonance environments to reduce radio frequency absorption and avoid substantial heating effects.

16 Claims, 16 Drawing Sheets

(56) References Cited

OTHER PUBLICATIONS

Angelone, et al., Computational Electromagnetic Analysis in a Human Head Model with EEG Electrodes and Leads Exposed to RF-Field Sources at 915 MHz and 1748 MHz, Radiat. Res., 2010, 174(1):91-100.
Arantes, et al., Performing Functional Magnetic Resonance Imaging in Patients With Parkinson's Disease Treated With Deep Brain Stimulation, Movement Disorders, 2006, 21(8):1154-1162.
Baker, et al., Evaluation of Specific Absorption Rate as a Dosimeter of MRI-Related Implant Heating, Journal of Magnetic Resonance Imaging, 2004, 20:315-320.
Baker, et al., Variability in RF-Induced Heating of a Deep Brain Stimulation Implant Across MR Systems, Journal of Magnetic Resonance Imaging, 2006, 24:1236-1242.
Bassen, et al., MRI-Induced Heating of Selected Thin Wire Metallic Implants—Laboratory and Computational Studies—Findings and New Questions Raised, Minimally Invasive Therapy, 2006, 15(2):78-86.
Bhidayasiri, et al., Bilateral Neurostimulation Systems Used for Deep Brain Stimulation: In Vitro Study of MRI-Related Heating at 1.5 T and Implications for Clinical Imaging of the Brain, Magnetic Resonance Imaging, 2005, 23:549-555.
Bonmassar, et al., Influence of EEG Electrodes on the BOLD fMRI Signal, Human Brain Mapping, 2001, 14:108-115.
Bonmassar, Resistive Tapered Stripline (RTS) in Electroencephalogram Recordings During MRI, IEEE Transactions on Microwave Theory and Techniques, 2004, 52(8):1-7.
Bonmassar, et al., PTFOS: Flexible and Absorbable Intracranial Electrodes for Magnetic Resonance Imaging, PLOS One, 2012, 7(9):e41187,11 pages.
Cabot, et al., Evaluation of the RF Heating of a Generic Deep Brain Stimulator Exposed in 1.5 T Magnetic Resonance Scanners, 2013, Bioelectromagnetics, 2013, 34(2):104-113.
Chou, Rf Heating of Metallic Implants During MRI, International EMF Conference, 2007, pp. 37-40.
Chu, Mechanical Properties of Suture Materials, An Important Characterization, Ann. Surg., 1981, 193(3):365-371.
Collins, et al., Signal-to-Noise Ratio and Absorbed Power as Functions of Main Magnetic Field Strength, and Definition of "90 degrees" RF Pulse for the Head in the Birdcage Coil, Magnetic Resonance in Medicine, 2001, 45:684-691.
Detti, et al., Assessment of Radiofrequency Self-Heating Around a Metallic Wire With MR T1-Based Thermometry, Magnetic Resonance in Medicine, 2011, 66:448-455.
D'Haese, et al., Clinical Accuracy of a Customized Stereotactic Platform for Deep Brain Stimulation After Accounting for Brain Shift, Stereotactic and Functional Neurosurgery, 2010, 88:81-87.
Dormont, et al., Neuroimaging and Deep Brain Stimulation, AJNR Am. J. Neuroradiol., 2010, 31:15-23.
Ehses, et al., MRI Thermometry: Fast Mapping of RF-Induced Heating Along Conductive Wires, Magnetic Resonance in Medicine, 2008, 60:457-461.
Elwassif, et al., Temperature Control at DBS Electrodes Using Heat Sink: Experimentally Validated Fem Model of DBS Lead Architecture, J. Neural Eng., 2012, 9(4):046009, 19 pages.
Fleming, et al., Overcoming Status Quo Bias in the Human Brain, PNAS, 2010, 107(13):6005-6009.
Gensler, et al., Mr Safety: Fast T1 Thermometry of the Rf-Induced Heating of Medical Devices, Magnetic Resonance in Medicine, 2012, 68:1593-1599.
Goldman, et al., Acquiring Simultaneous Eeg and Functional Mri, Clinical Neurophysiology, 2000, 111(11)1974-1980.
Henderson, et al., Permanent Neurological Deficit Related to Magnetic Resonance Imaging in a Patient With Implanted Deep Brain Stimulation Electrodes for Parkinson's Disease: Case Report, Neurosurgery, 2005,57(5):E1063, 4 pages.
Kozlov, et al., Fast MRI Coil Analysis Based on 3-D Electromagnetic and RF Circuit Co-Simulation, Journal of Magnetic Resonance, 2009, 200:147-152.
Kundu, et al. Integrated Strategy for Improving Functional Connectivity Mapping Using Multiecho fMRI, PNAS Early Edition, 2013, 6 pages.
Ladd, et al., Reduction of Resonant RF Heating in Intravascular Catheters Using Coaxial Chokes, Magnetic Resonancein Medicine, 200-0, 43:615-619 2000.
Lemieux, et al., Event-Related fTV1RIWith Simultaneous and Continuous EEG: Description of the Method and Initial Case Report, NeuroImage, 2001, 14:780-787.
Makris, et al., MRI-Based Anatomical Model of the Human Head for Specific Absorption Rate Mapping, Med. Biol. Eng. Comput., 2008, 46(12):1239-1251.
Massire, et al., Thermal Simulations in the Human Head for High Field MRI Using Parallel Transmission, Journal of Magnetic Resonance Imaging, 2012, 35:1312-1321.
Mattei, et al., Complexity of MRI Induced Heating on Metallic Leads: Experimental Measurements of 374 Configurations, BioMedical Engineering Online, 2008, 7:11, 16 pages.
Medtronic, MRI Guidelines for Medtronic Deep Brain Stimulation Systems, Copyright Medtronic, Inc. 2014, 44 pages.
Medtronic, System Eligibility Battery Longevity, Neurostimulation Systems for Deep Brain Stimulation, Reference Manual, Copyright Medtronic, Inc. 2014, 48 pages.
Merilampi, et al., the Effect of Conductive Ink Layer Thickness on the Functioning of Printed UHF RFID Antennas, Proceedings of the IEEE, 2010, 98(9):1610-1619.
Mullinger, et al., Poststimulus Undershoots in Cerebral Blood Flow and Bold fMRI Responses are Modulated by Poststimulus Neuronal Activity, PNAS, 2013, 110(33):13636-13641.
Osborne, et al., Looking Beyond Silicon, Science, 2010, 327:1595.
Rezai, et al., Neurostimulation Systems for Deep Brain Stimulation: in Vitro Evaluation of Magnetic Resonance Imaging-Related Heating at 1.5 Tesla, Journal of Magnetic Resonance Imaging, 2002, 15:241-250.
Schurig, et al., Metamaterial Electromagnetic Cloak at Microwave Frequencies, Science, 2006, 314:977-980.
Shellock, et al., MRI Safety Update 2008: Part 2, Screening Patents for MRI, AJR, 2008, 191:1140-1149.
Shrivastava, et al., Effect of the Extracranial Deep Brain Stimulation Lead on Radiofrequency Heating at 9.4 Tesla (400.2 MHz), Journal of Magnetic Resonance Imaging, 2010, 32:600-607.
Shrivastava, et al., Heating Induced Near Deep Brain Stimulation Lead Electrodes During Magnetic Resonance Imaging With a 3T Transceive vol. Head Coil, Phys. Med. Biol., 2012, 57(17):5651-5665.
Spiegel, et al., Transient Dystonia Following Magnetic Resonance Imaging in a Patient With Deep Brain Stimulation Electrodes for the Treatment of Parkinson Disease, J. Neurosurg., 2003, 99:772-774.
Toda, et al., A Novel Composite Targeting Method Using High-Field Magnetic Resonance Imaging for Subthalamic Nucleus Deep Brain Stimulation, J. Neurosurg., 2009, 111:737-745.
Wu, et al., The Cylindrical Antenna With Nonreflecting Resistive Loading, IEEE Transactions on Antennas and Propagation, 1965, 13:369-373.
Yeo, et al., Local Specific Absorption Rate in High-Pass Birdcage and Transverse Electromagnetic Body Coils for Multiple Human Body Models in Clinical Landmark Positions at 3T, Journal of Magnetic Resonance Imaging, 2011, 33:1209-1217.
Acheson, Technical Data Sheet, Electrodag 479SS, Aug. 2010, 2 pages.
Bonmassar, et al., Specific Absorption Rate in a Standard Phantom Containing a Deep Brain Stimulation Lead at 3 Tesla MRI, 2013 6th Annual International IEEE/EMBS Conference on Neural Engineering, pp. 747-750.
Buchli, et al., Heating Effects of Metallic Implants by MRI Examinations, Magnetic Resonance in Medicine, 1988, 7(3):255-261.
Chhabra, et al., Safety of Magnetic Resonance Imaging of Deep Brain Stimulator Systems: A Serial Imaging and clinical Retrospective Study, Journal of Neurosurgery, 2010, 112(3):497-502.

(56) References Cited

OTHER PUBLICATIONS

Chou, et al., Carbon-Loaded Teflon Electrodes for Chronic EEG Recordings in Microwave Research, Journal of Microwave Power, 1979, 14(4):399-404.
Chou, et al., RF Heating of Implanted Spinal Fusion Stimulator During Magnetic Resonance Imaging, 1997, IEEE Transactions on Biomedical Engineering, 1997, 44(5):367-373.
Dang, et al., Giant Dielectric Permittivities in Functionalized Carbon-Nanotube/Electroactive-Polymer Nanocomposites, Advanced Materials, 2007, 19(6):852-857.
Fraix, et al., Effects of Magnetic Resonance Imaging in Patients With Implanted Deep Brain Stimulation Systems, Journal of Neurosurgery, 2010, 113(6):1242-1245.
Gaylord, et al., Analysis and Applications of Optical Diffraction by Gratings, Proceedings of the IEEE, 1985, 73(5):894-937.
Gonzalez, et al., A Flexible Perforated Microelectrode Array Probe for Action Potential Recording in Nerve and Muscle Tissues, Journal of Neuroscience Methods, 1997, 72(2):189-195.
Gray, et al., Simple Design Changes to Wires to Substantially Reduce MRI-Induced Heating at 1.5 T: Implications for Implanted Leads, Magnetic Resonance Imaging, 2005, 23(8):887-891.
Harlow, Why Breakwaters Break, Oceans '88. A Partnership of Marine Interests. Proceedings, IEEE 1988, pp. 1250-1252.
Harmuth, On the Effect of Absorbing Materials on Electromagnetic Waves With Large Relative Bandwith, IEEE Transactions on Electromagnetic Compatibility, 1983, EMC-25(1):32-39.
Hassler, et al., Characterization of Parylene C as an Encapsulation Material for Implanted Neural Prostheses, Journal of Biomedical Materials Research Part B: Applied Biomaterials, 2010, 93B(1):266-274.

Kanda, A Relatively Short Cylindrical Broadband Antenna with Tapered Resistive Loading for Picosecond Pulse Measurements, IEEE Transactions on Antennas and Propagation, 1978, AP-26(3), 439-447.
Kato, et al., Composition of MRI Phantom Equivalent to Human Tissues, Medical Physics, 2005, 32(10):3199-3208.
Mattei, et al., Temperature and SAR Measurement Errors in the Evaluation of Metallic Linear Structures Heating During MRI Using Fluoroptic Probes, Physics in Medicine and Biology, 2007, 52(6):1633-1646.
Mohsin, et al., MRI-Induced Heating of Deep Brain Stimulation Leads, Physics in Medicine & Biology, 2008, 53 (20):5745-5756.
Neufeld, et al., Measurement, Simulation and Uncertainty Assessment of Implant Heating During MRI, Physics in Medicine and Biology, 2009, 54(13):4151-4169.
Peng, Rigorous Formulation of Scattering and Guidance by Dielectric Grating Waveguides: General Case of Oblique Incidence, Journal of the Optical Society of America A, 1989, 6(12):1869-1883.
Ratner, et al., Analysis of Biomedical Polymer Surfaces: Polyurethanes and Plasma-Deposited Thin Films, Clinical Materials, 1993, 13(1-4):71-84.
Sharan, et al., MR Safety in Patients With Implanted Deep Brain Stimulation Systems (DBS), Acta Neurochir Suppl, 2003, 87:141-145.
Volkmann, et al., Introduction to the Programming of Deep Brain Stimulators, Movement Disorders, 2002, 17(Suppl. 3):S181-S187.
Yang, et al., Scattering Analysis of Dielectric Periodic Structures by an Oblique Incidence, International Journal of Infrared and Millimeter Waves, 2000, 21(11)1807-1823.
Guy, Biophysics—Energy Absorption and Distribution, Agard Lecture Series, 78, 1975, 14, pp. 4-1 thru 4-14.

\* cited by examiner

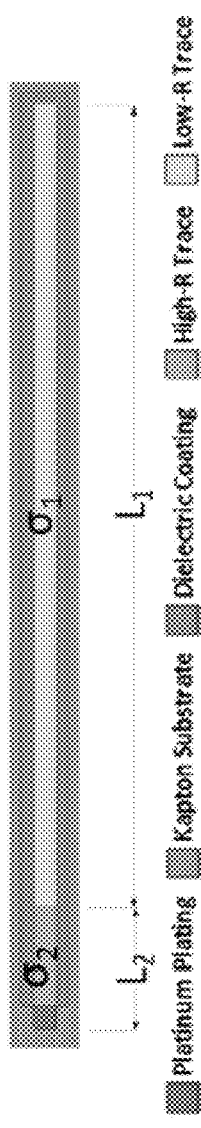
Figure 3A
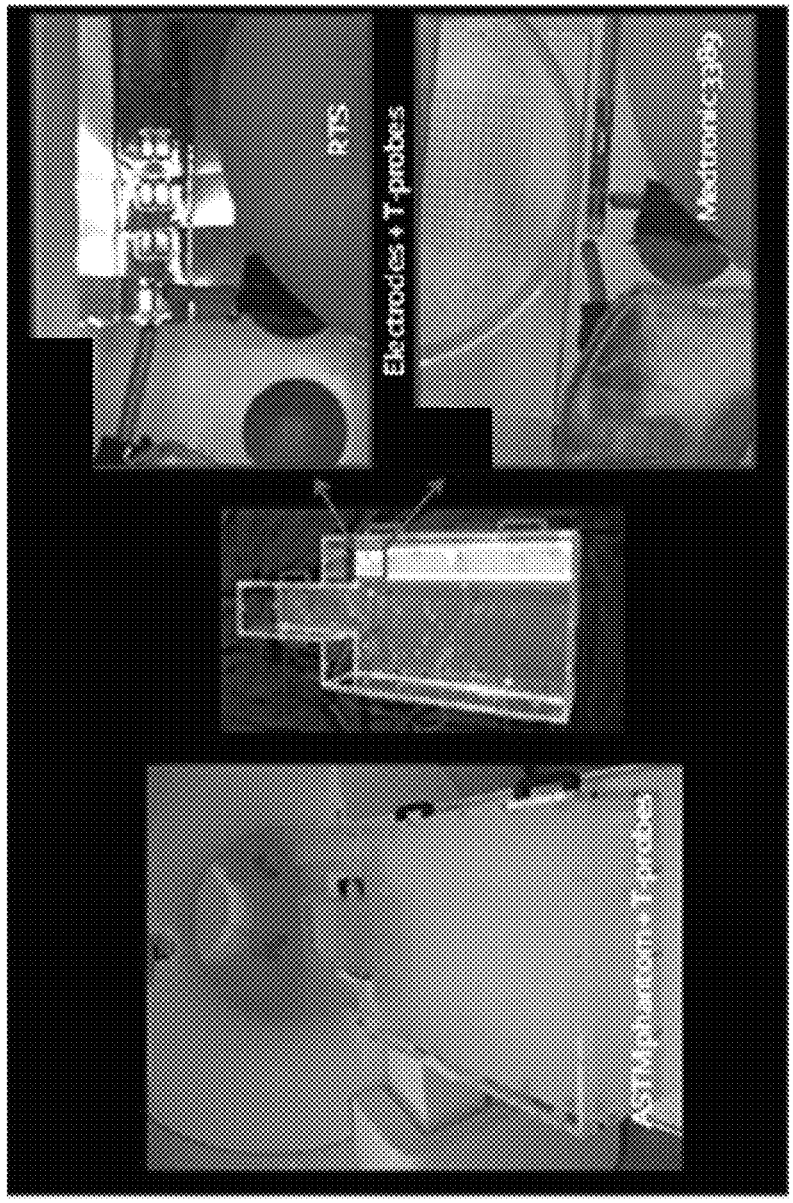
Figure 3B
Figure 3C
Figure 3D

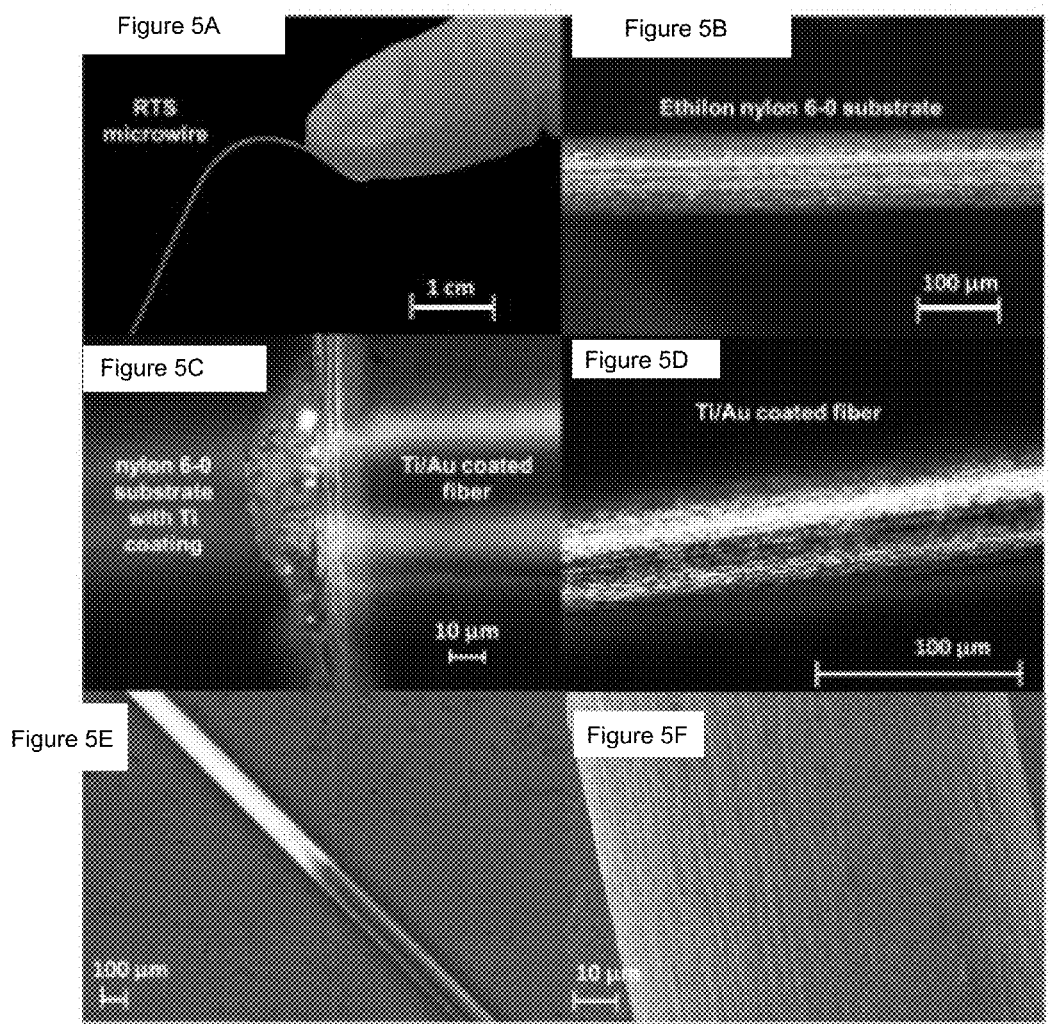

MRI COMPATIBLE LEADS FOR A DEEP BRAIN STIMULATION SYSTEM

CROSS-REFERENCES TO RELATED APPLICATIONS

This application claims priority from U.S. Patent Application No. 62/048,534 filed Sep. 10, 2014 and U.S. Patent Application No. 62/132,671 filed Mar. 13, 2015.

STATEMENT REGARDING FEDERALLY SPONSORED RESEARCH

This invention was made with government support under grants U01-NS075026 (NIH/NINDS), 1R21EB016449-01A1 (NIH/NIBIB), and the National Center for Research Resources (P41-RR14075). The government has certain rights in the invention.

BACKGROUND OF THE INVENTION

1. Field of the Invention

The invention relates to a lead for an implanted medical device in which the lead includes a wire for placing an electrical signal source in electrical communication with an electrode at a distal tip of the lead. The lead is substantially transparent to radio frequency waves in clinically-applicable magnetic resonance environments to avoid radio frequency heating effects.

2. Description of the Related Art

Magnetic resonance imaging (MRI) for patients with [1] neurostimulators has advantages and limitations. Implanted medical devices such as cardioverter-defibrillators, pacemakers, spinal cord stimulators, and deep brain stimulation (DBS) have become well-accepted therapeutic options to treat a wide range of medical conditions and contribute to improved quality of life. [Ref. 1] Many patients with implanted devices can benefit from MRI, which is the diagnostic tool of choice for monitoring structural changes in the body, as well as diagnosing many common illnesses including cancer, cardiovascular disease, and trauma. Additionally, functional MRI is becoming more prevalent in assessing brain function and cognitive disorders [Ref. 2,3]. However, approximately 300,000 patients with implanted or partially implanted medical devices are denied MRI each year because of safety concerns [Ref. 4]. A major concern when performing MRI examinations in patients with electrically conductive implants is the increase in induced currents ("antenna effect") along conductive leads in the body that are exposed to the radiofrequency (RF) waves of the MRI. The increase in current flow into the tissue at the point of contact with the lead (i.e., the electrodes) causes a large amount of RF energy to be absorbed in the tissue, which in turn causes surges in temperatures that can lead to injury [Ref. 5-12]. Temperature increases of up to 25° C. were measured near a DBS 3389 lead (Medtronic, Inc., Minneapolis, Minn.) in an in-vitro gel phantom at 1.5 T MRI [Ref. 13]. Additionally, increases of up to 30° C. were measured with the Medtronic 3389 lead in a swine head at 9.4 T [Ref. 14]. More importantly, two cases of serious, permanent neurological injury, after MRI exposure at 1.0 T in patients with DBS implants, have been reported [Ref. 15,16]. In both cases the manufacturer guidelines were not followed and in one case the patient developed paralysis following MRI examination [Ref. 16]. The lack of access to MRI is expensive to society because patients are denied the benefits of screening and accurate diagnosis.

A class of implantable devices—defined as "MR Conditional" [Ref. 17]—have been shown to pose no known hazards in the MRI environment when operated with specified conditions. For example, the Activa® DBS system (Medtronic, Inc., Minneapolis, Minn.) is approved for use in MRI [Ref. 18] with several conditions [Ref. 19], including limited static and gradient magnetic fields, use of low power sequences, and specific RF coils. These conditions, however, are restrictive. The limit for power absorbed by the patient's head is over 30-fold less than typical values allowed, which restricts the number, the type, and quality of MRI scans that can be performed in a given session. The most commonly used transmit body coils are not allowed, excluding the possibility of using MRI to diagnose morbidities in the human torso (e.g., breast cancer, back pain). Additionally, the conditions exclude the use of 3.0 T MRI systems, which are predominately used in clinical [Ref. 20] and research applications [Ref. 21,22].

Therefore, a need exists for an improved a lead for an implanted medical device wherein the lead is substantially transparent to radio frequency waves in clinically-applicable magnetic resonance environments to avoid radio frequency heating effects.

SUMMARY OF THE INVENTION

Clinical electrical stimulation systems—such as pacemakers and deep brain stimulators (DBS)—are an increasingly common therapeutic option to treat a large range of medical conditions. Despite their remarkable success, one of the significant limitations of these medical devices is the limited compatibility with magnetic resonance imaging (MRI), a standard diagnostic tool in medicine. During an MRI exam, the leads used with these devices, implanted in the body of the patient, act as an electric antenna potentially causing a large amount of energy to be absorbed in the tissue, which can lead to heat-related injury. This disclosure presents a novel lead design that reduces the antenna effect and allows for decreased tissue heating during MRI. The parameters of the lead wire design were determined by a combination of computational modeling and experimental measurements. The results of these simulations were used to build lead wires, which were tested in a gel phantom during an MRI scan. Measurement results showed a three-fold decrease in heating when compared to a commercially available DBS lead. Accordingly, the lead of the present disclosure allows a significantly increased number of patients with medical implants to have safe access to the diagnostic benefits of MRI.

The present disclosure provides a lead for an implanted medical device in which the lead is adapted for electrical communication with an electrical signal source and has a distal tip with an electrode. The lead comprises a wire adapted to be placed in electrical communication with electrode. The wire includes: (i) a core comprising a polymeric material, and (ii) a metallic layer surrounding an outer surface of the core. The metallic layer includes a first section having a first thickness and a second section having a second thickness, wherein the first thickness is greater than the second thickness. The lead is substantially transparent to radio frequency waves in clinically-applicable magnetic resonance environments to reduce radio frequency absorption and avoid substantial heating effects.

The present disclosure also provides a lead for an implanted medical device in which the lead is adapted for electrical communication with an electrical signal source and has a distal tip with an electrode. The lead comprises a wire adapted to be placed in electrical communication with electrode. The wire includes: (i) a core comprising a polymeric material, and a metallic layer surrounding an outer surface of the core, wherein the metallic layer includes a discontinuity in electrical conductivity along its axial length. The lead is substantially transparent to radio frequency waves in clinically-applicable magnetic resonance environments to reduce radio frequency absorption and avoid substantial heating effects.

These and other features, aspects, and advantages of the present invention will become better understood upon consideration of the following detailed description, drawings, and appended claims.

Figure if shows a resistive tapered striplines (RTS) design and simulation setup, specifically, placement of the wire inside the phantom. The location was chosen because of the high magnitude of incident electric field.

Figure 2A:
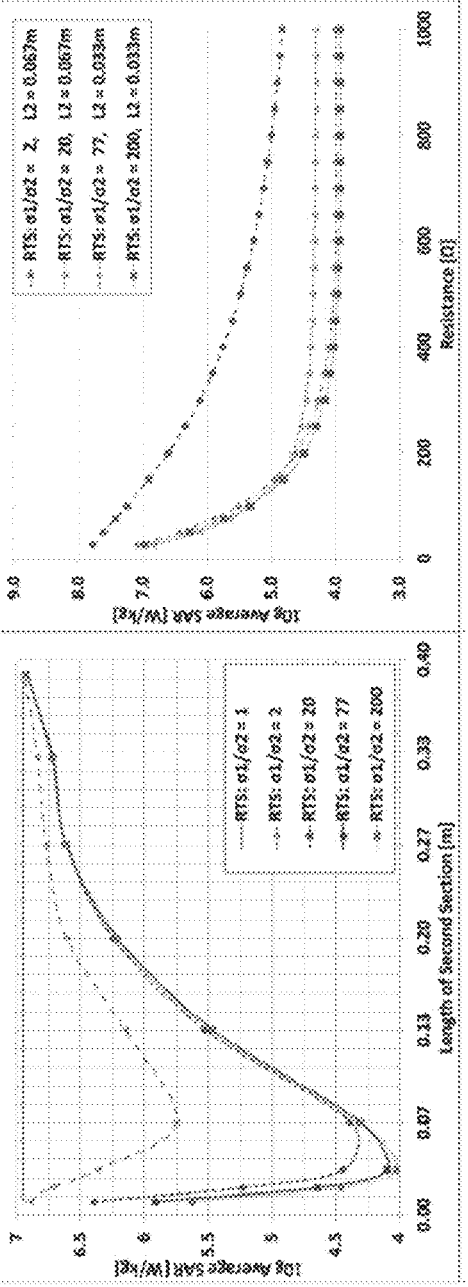

FIG. 2a shows one optimal RTS design in phantom, specifically, a 10 g-avg. SAR inside the phantom at a distance of 0.1 mm from the electrode obtained by varying the length ($L_2$) of the second section (see Methods of Example 1). Plots include different conductivity ratios for the two layers. In all cases the total resistance of the lead was R=400$\Omega$.

Figure 2B:
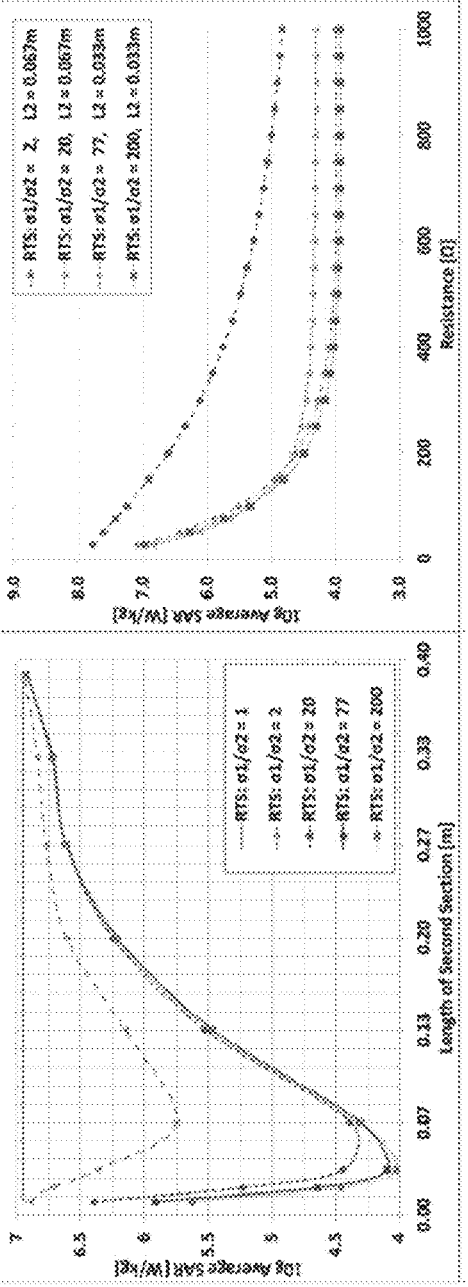

FIG. 2b shows one optimal RTS design in phantom, specifically, a 10 g-avg. SAR at the same point obtained by varying the total resistance of the lead. Plots include four combinations of conductivity ratios of the two layers and length $L_2$ of the second section.

Figure 2C:
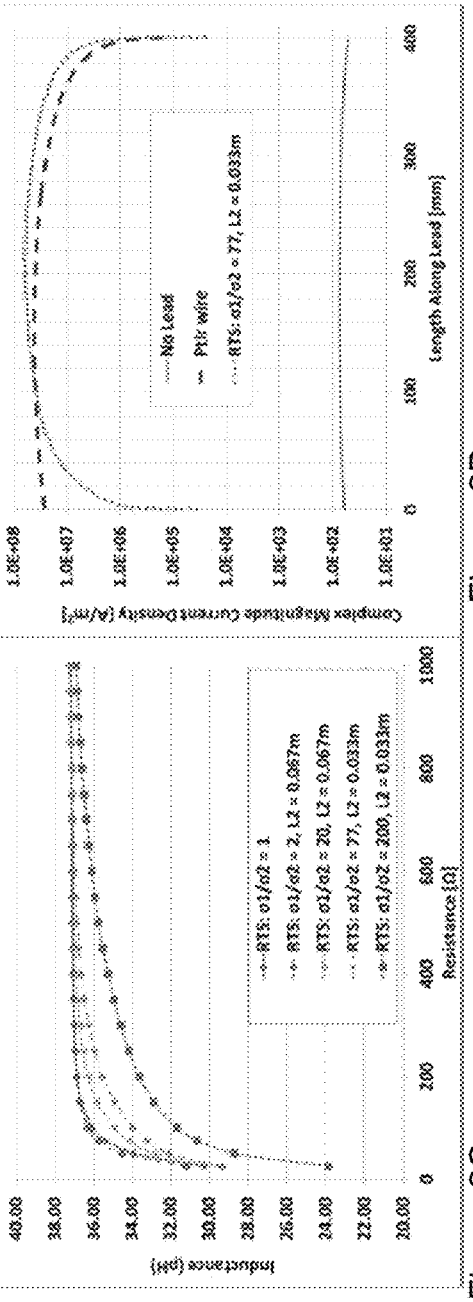

FIG. 2c shows one optimal RTS design in phantom, specifically, a maximum inductance of the RTS varying the total resistance of the lead. Plots include five combinations of conductivity ratios of the two layers and length $L_2$ of the second section.

Figure 2D:
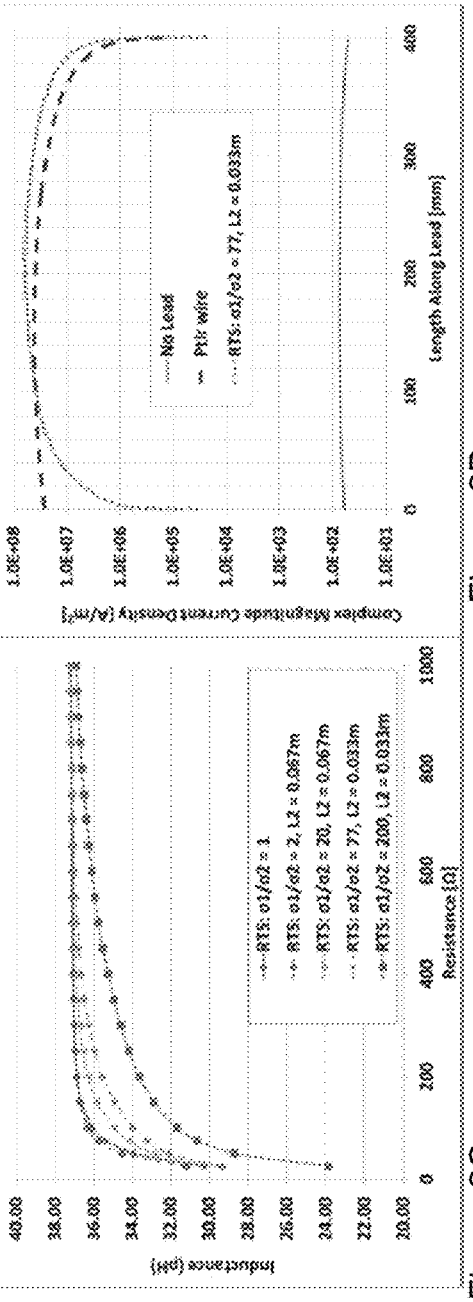

FIG. 2d shows one optimal RTS design in phantom, specifically, an amplitude of induced current inside the lead with the PtIr wire, with the RTS lead selected for prototype manufacturing (right) and in the corresponding volume of the ASTM phantom without lead. The RTS lead allowed for a 37-fold decrease in induced current at the electrode (length along lead=0 mm). In all cases, the total length of the leads was 40 centimeters.

Figure 1A:
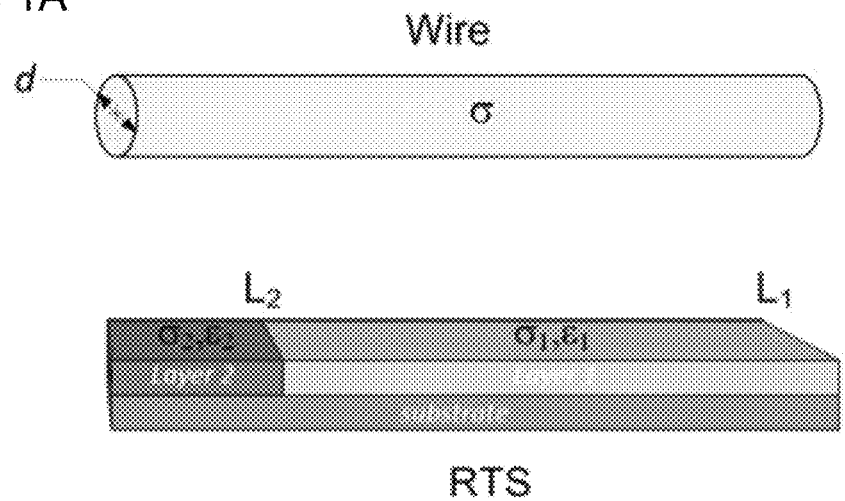
FIG. 1a shows a resistive tapered striplines (RTS) design and simulation setup, specifically, a schematic of the PtIr wire (diameter d=100 mm, electrical conductivity $\sigma$=4.0× $10^6$ S/m) and the two-layer RTS design (electrical conductivity $\sigma_1$ and $\sigma_2$, permittivity $\varepsilon_1$ and $\varepsilon_2$, length $L_1$ and $L_2$) used for Example 1.
Figure 1B:
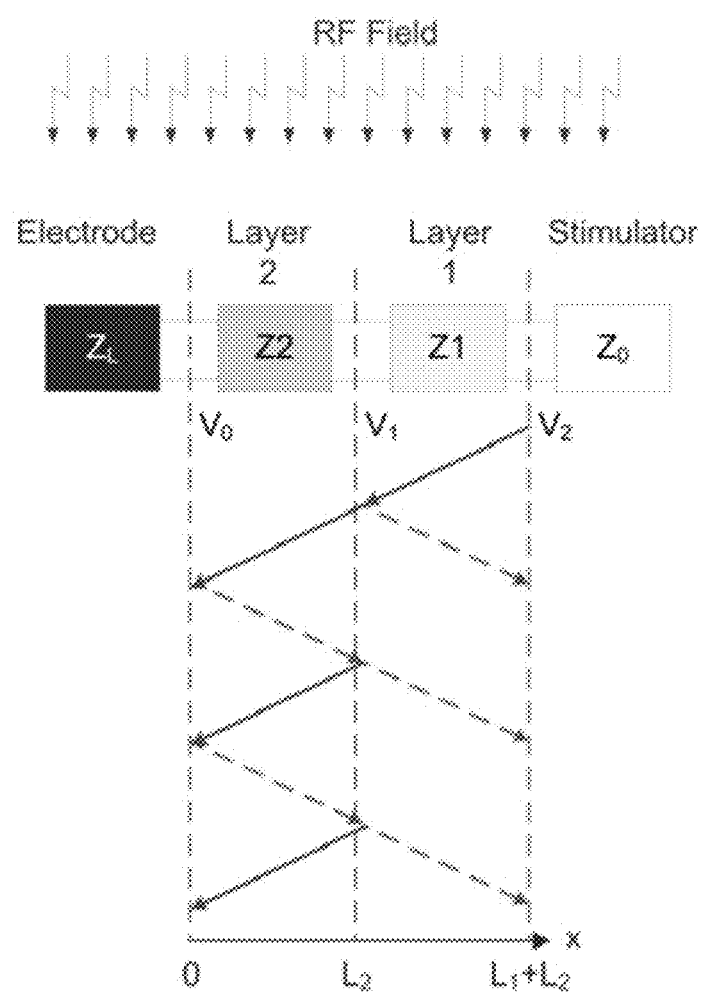
FIG. 1b shows a resistive tapered striplines (RTS) design and simulation setup, specifically, an equivalent circuit used to model the RTS implant with four sections: stimulator, two layer transmission line, and electrode/tissue interface. The incident RF field induces currents along the implants, which are reflected depending on neighboring section's mismatched impedance ($Z_0$, $Z_1$, $Z_2$, and $Z_L$). The resulting voltage amplitude at each interface ($V_0$, $V_1$, and $V_2$) was generated by the induced current.
Figure 1C:
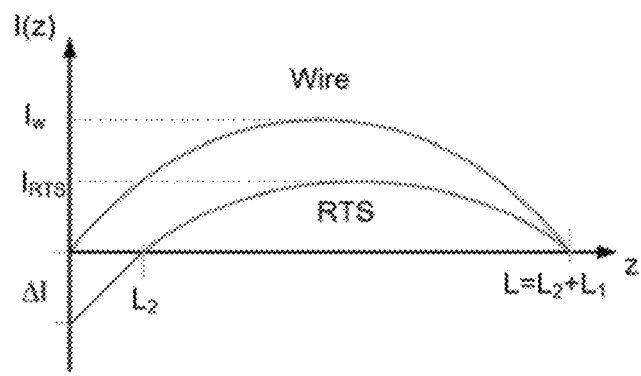
FIG. 1c shows a resistive tapered striplines (RTS) design and simulation setup, specifically, RF-induced currents along the two wires. The current in the metallic conductor forms a standing wave with high peaks in amplitude ($I_w$); conversely, the effect of RTS design is two-fold: (a) reduces the average induced currents ($I_{RTS}$) along the implant by worsening the antenna performance, and (b) reduces the induced current at the electrode ($\Delta I$) by introducing scattering within the implant.
Figure 1D:
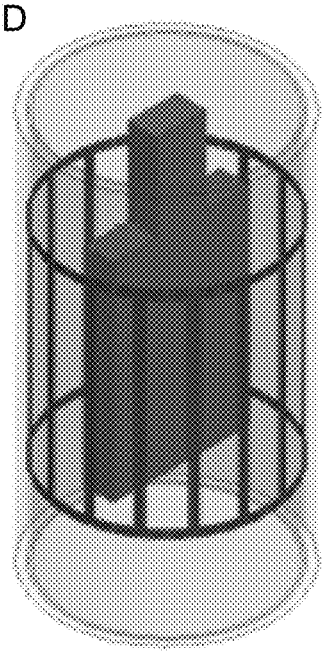
FIG. 1d shows a resistive tapered striplines (RTS) design and simulation setup, specifically, a CAD Model used in the numerical simulations, including a 16-leg high-pass birdcage body coil with RF shield, coil former and ASTM phantom.
Figure 1E:
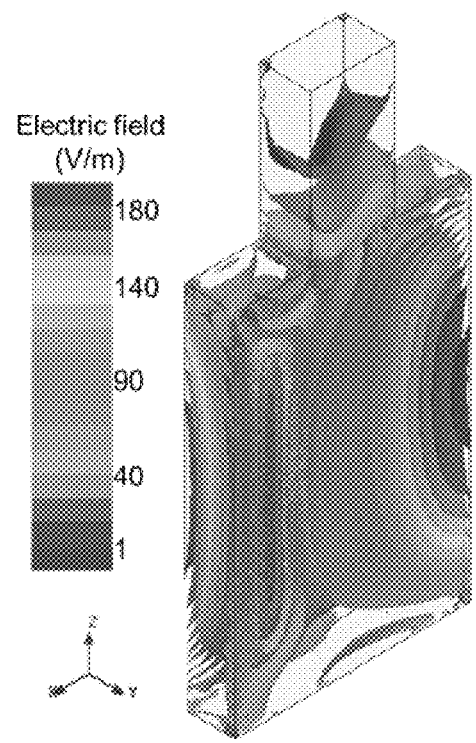
FIG. 1e shows a resistive tapered striplines (RTS) design and simulation setup, specifically, a 3D plot of electric field magnitude at the Larmor frequency ($f_0$=128 MHz) in the ASTM phantom model used in the simulations. Results were normalized to a power level yielding a whole-body SAR=2 W/kg (i.e., Normal Operating Mode [Ref. 41]).
Figure 1F:
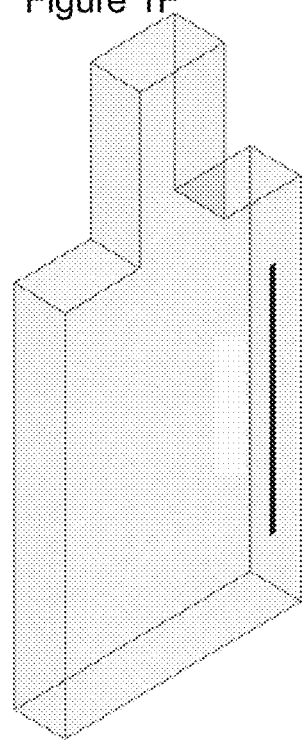
Figure 2E:
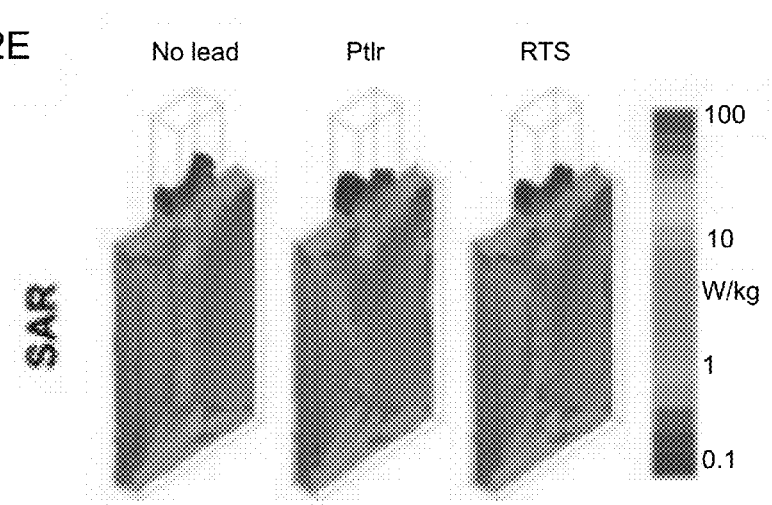

FIG. 2e shows one optimal RTS design in phantom, specifically, numerical simulation results at 128 MHz calculated with a finite element method using the geometry shown in FIGS. 1d and 1f and with either a single-electrode PtIr wire or an RTS lead. 10 g-avg. SAR in the ASTM phantom without lead (left), with the PtIr wire (middle), and with the RTS design that was selected for prototype manufacturing (right). Values were normalized to whole-body SAR of 2 W/kg.

Figure 2F:
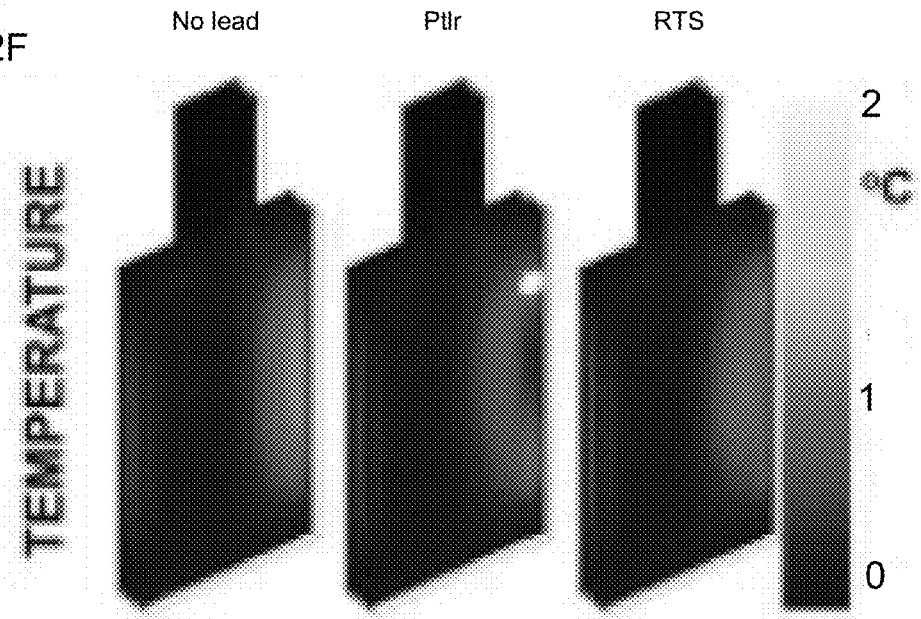

FIG. 2f shows one optimal RTS design in phantom, specifically, temperature maps for 15 minutes of continuous SAR exposure for the same three cases described in FIG. 2e. Simulations showed that the RTS lead is transparent to the incident RF field and generated similar temperature increase (up to 0.9° C.) compared with the ASTM phantom without lead. By contrast, the PtIr wire generated a temperature increase up to 12° C. near the electrode (it is noted that the color bar threshold was set to 2° C. to improve visualization.) FIG. 3a shows temperature measurements of an RTS design, specifically, a schematic of the two-layer RTS design (electrical conductivity $\sigma_1$ and $\sigma_2$, permittivity: $\sigma_1$ and $\varepsilon_2$, length $L_1$ and $L_2$ used for Example 1.

FIG. 3b shows temperature measurements of an RTS design, specifically, an ASTM phantom in the 3 T system used for the temperature measurements. The lead was placed laterally on the right side of the phantom, on a white plastic support.

FIG. 3c shows temperature measurements of an RTS design, specifically, detail showing the temperature sensors placed near the manufactured RTS prototype. The four PtIr electrodes are visible, with the probe located on top of one of them.

FIG. 3d shows temperature measurements of an RTS design, specifically, a commercial lead used for the comparison and placement of the temperature probes near the electrodes. The probes were placed perpendicular to the lead to minimize error accuracy [Ref. 53].

Figure 3E:
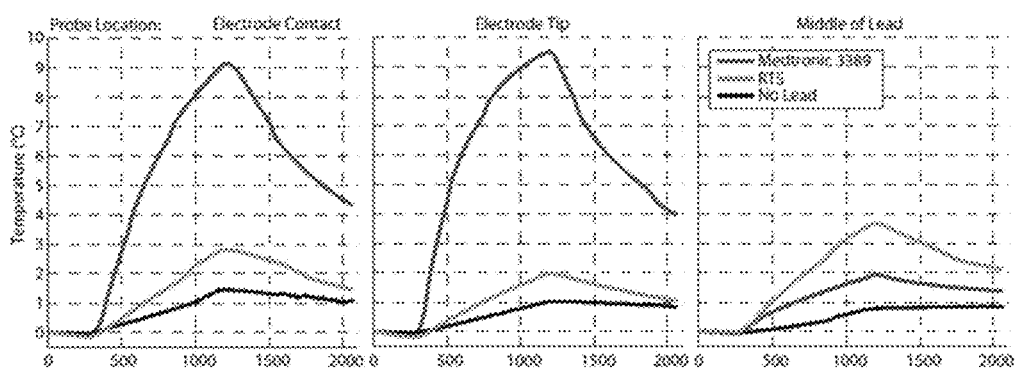

FIG. 3e shows temperature measurements of an RTS design, specifically, results of temperature measurements at three different positions within the phantom without lead, with a Medtronic 3389 lead, and with the RTS lead.

Figure 3F:
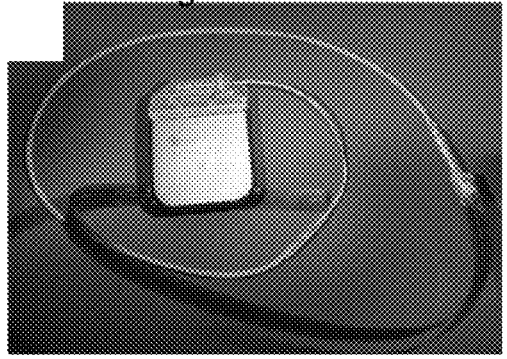

FIG. 3f shows temperature measurements of an RTS design, specifically, the configuration of battery testing with RTS lead.

Figure 3G:
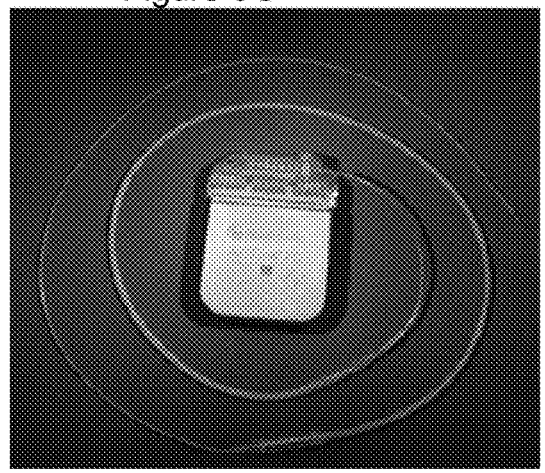

FIG. 3g shows temperature measurements of an RTS design, specifically, a configuration of testing with the Medtronic 3389 lead. Each of the two leads was connected to a commercial DBS IPG system via an extension. The full system (i.e., IPG, extension, and leads) was immersed in physiologic solution for both the RTS and the commercial lead. Battery consumption was tested over a four-week period for both the Medtronic 3389 and the RTS leads. Both leads showed a 0.005 V initial drop in battery voltage, followed by a constant level over the time evaluated.

Figure 4A:
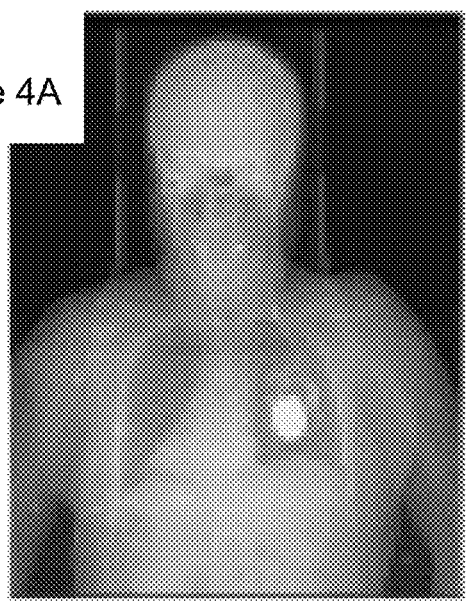

FIG. 4a shows an RTS design in a human body model, specifically, an X-Ray image of a patient with an implanted bilateral DBS system. A head holder, the implantable pulse generator (IPG) in the thorax, and the two leads are visible.

Figure 4B:
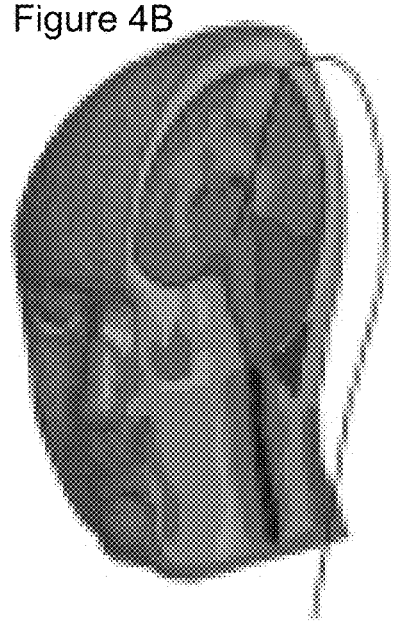

FIG. 4b shows an RTS design in a human body model, specifically, an anatomical model of a human body with implanted DBS lead used for numerical simulations.

Figure 4C:
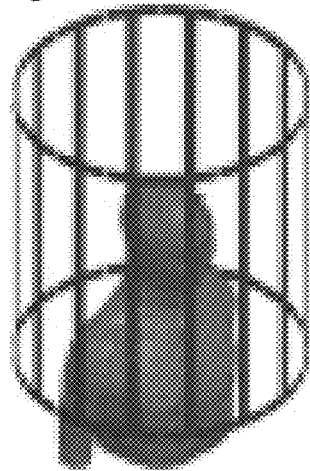

FIG. 4c shows an RTS design in a human body model, specifically, a model of the human body inside the RF body coil.

Figure 4D:
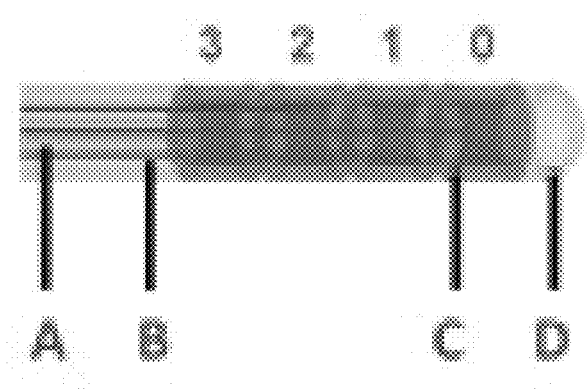

FIG. 4d shows an RTS design in a human body model, specifically, a model of the lead, including the lumen (A), the four RTS wires (B), the four electrodes numbered as in the Medtronic 3389 (i.e., 0-3) (C), and the insulation (D).

Figure 4E:
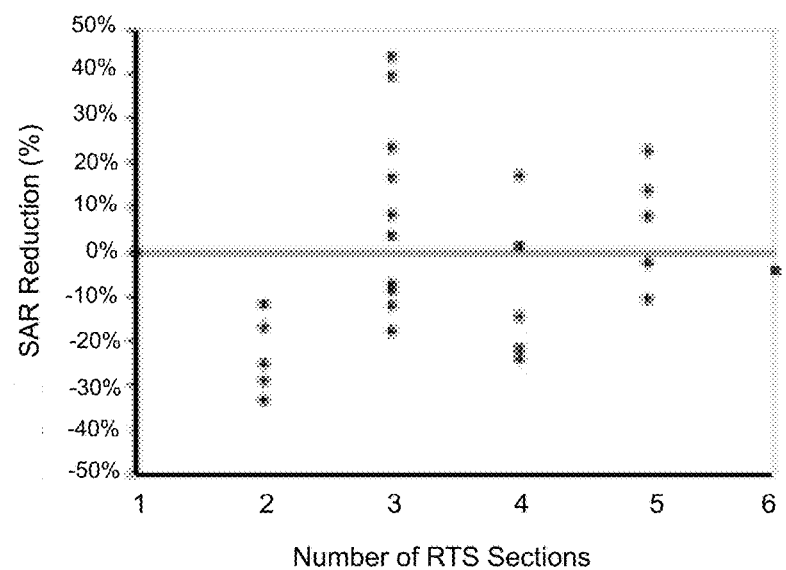

FIG. 4e shows an RTS design in a human body model, specifically, a graph showing the results of analysis of 10 g-avg. SAR reduction with respect to different RTS configurations (i.e., from two to six sections.)

Figure 4F:
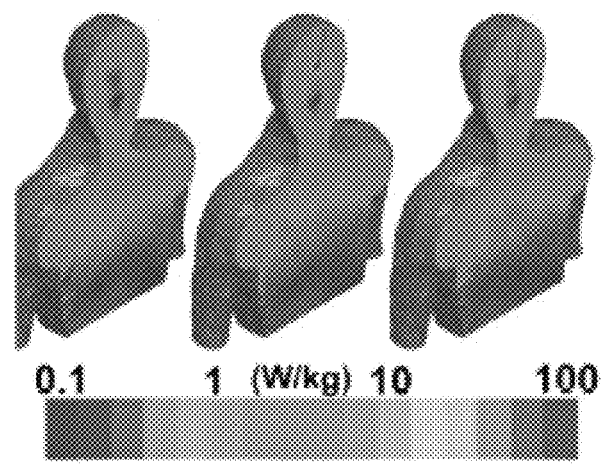

FIG. 4f shows an RTS design in a human body model, specifically, a numerical simulation results showing a coronal view of power absorption in the human body model without implant (left), with PtIr lead (middle), and with RTS lead (right). The increase of power near the electrode for the PtIr lead is clearly visible. By contrast, the RTS wire is "RF-transparent" to the RF field (i.e., the map is similar to the case without the lead).

Figure 4G:
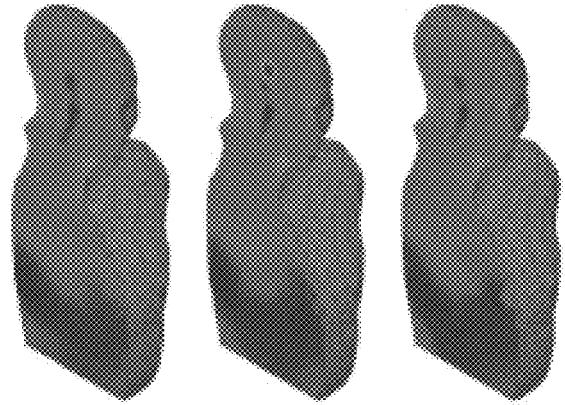

FIG. 4g shows an RTS design in a human body model, specifically, a sagittal view of the same results as in FIG. 4f.

FIG. 5a shows physical vapor deposition (PVD)-based manufacturing of a wire-design RTS prototype, specifically, two-layer RTS microwire. The RTS (80 mm diameter) was built with an Ethilon® 6-0 nylon suture used as a substrate and coated with a Ti/Au layer.

FIG. 5b physical vapor deposition (PVD)-based manufacturing of a wire-design RTS prototype, specifically, an optical microscope (OM) image of the Ethilon® 6-0 nylon suture used as a substrate to build the RTS microwire. The steep transition between the two RTS layers—necessary for the maximizing the mismatched impedance and the scattering within the RTS fiber (see FIG. 1b)—is clearly visible.

FIG. 5c physical vapor deposition (PVD)-based manufacturing of a wire-design RTS prototype, specifically, an OM image of the interface between the two RTS layers.

FIG. 5d physical vapor deposition (PVD)-based manufacturing of a wire-design RTS prototype, specifically, an OM image of microwire fully coated with 100/150 nm of Ti/Au.

FIG. 5e physical vapor deposition (PVD)-based manufacturing of a wire-design RTS prototype, specifically, a scanning electron microscope (SEM) image of the RTS microwire.

FIG. 5f physical vapor deposition (PVD)-based manufacturing of a wire-design RTS prototype, specifically, an SEM view, with increased magnification, of the Au coating of the RTS fiber showing the characteristic fibrous surface of the Ethilon® nylon substrate.

Figure 6:
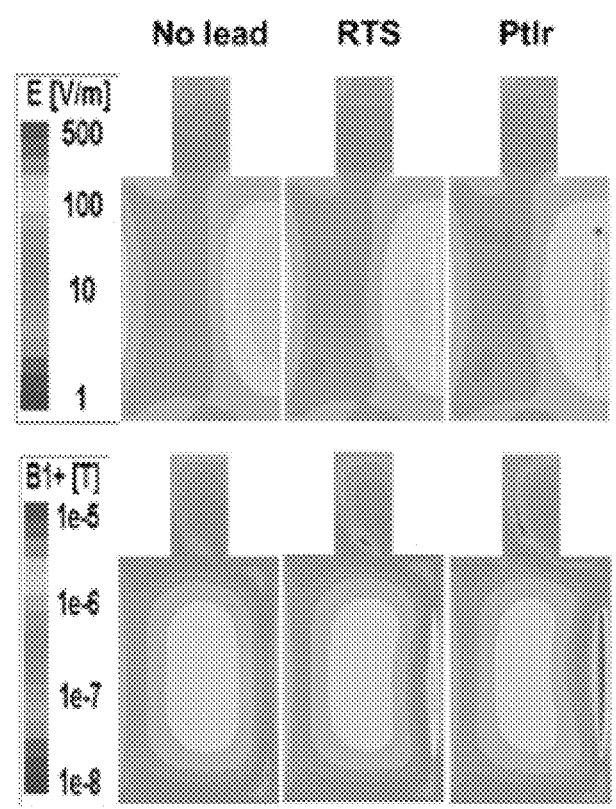

FIG. 6 shows electromagnetic simulations. Maps of (top) electric field and (bottom) $B_1^+$ field magnitude in the coronal (XZ) plane of the ASTM phantom at the isocenter of the lead. The $B_1^+$ field is the circularly polarized component of the magnetic field used to elicit the MRI signal ENREF_37 [Ref. S36]. Three cases are presented: (1st column from the left) phantom model without lead, (2nd column) with the selected RTS lead (i.e., $L_1$=0.367 m, $L_2$=0.033 m, $\sigma_1$=1.968×10$^6$ S/m, and $\sigma_2$=25.61·×10$^3$ S/m), and (3rd column) with a PtIr wire (100 µm diameter, 40 cm long). The top row shows the magnitude of the electric field at the computed frequency. The electric field peaks near the electrode and was maximum for the PtIr lead (3rd column), whereas it was much lower with the RTS (2nd column) and the ASTM phantom without lead (1st column). The second row shows the magnitude of $B_1$ field. The ASTM phantom without lead is the reference and any change in $B_1^+$ field near the lead when introducing the implant into the phantom with respect to the reference implies distortions in the field homogeneity.

Figure 7:
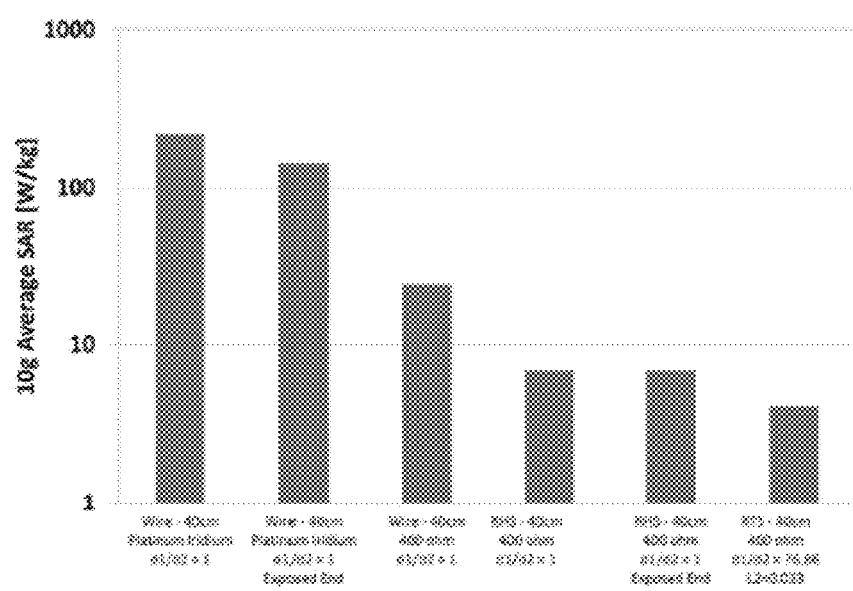

FIG. 7 shows the effect of lead configuration on 10 g-avg. SAR. The histogram shows 10 g-avg. SAR in the phantom at 0.1 mm from the electrode calculated with different lead configurations. The 10 g-avg. SAR varied with shape (i.e., wire vs. thin) and conductivity (homogeneous vs. RTS). These results illustrate that—with the configurations evaluated—wires produce larger peak SAR than thin leads. Additionally, the RTS design allowed for lower peak SAR when compared with a resistively homogeneous (i.e., $\sigma_1/\sigma_2$=1) thin stripline.

Figure 8:
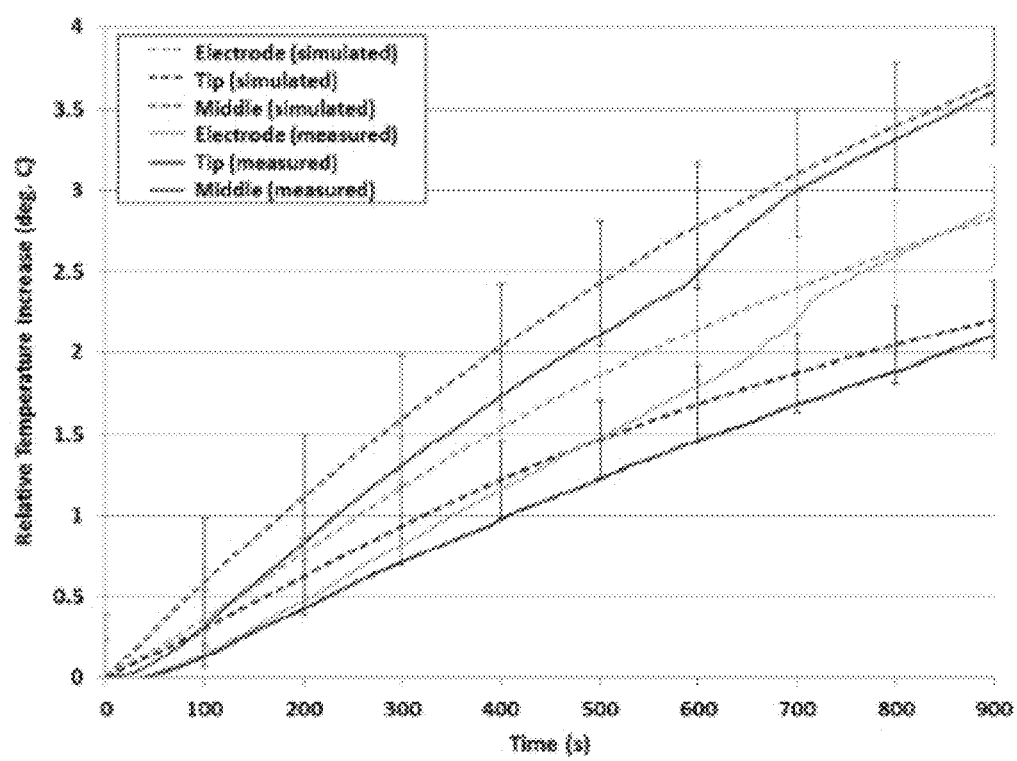

FIG. 8 shows temperature measurements in MRI vs. numerical simulations.

Temperature simulations with standard error as computed by the model used for the RTS design compared with the temperature changes measured in the MRI scanner. Simulations and measurements agreed within the standard error.

Figure 9:
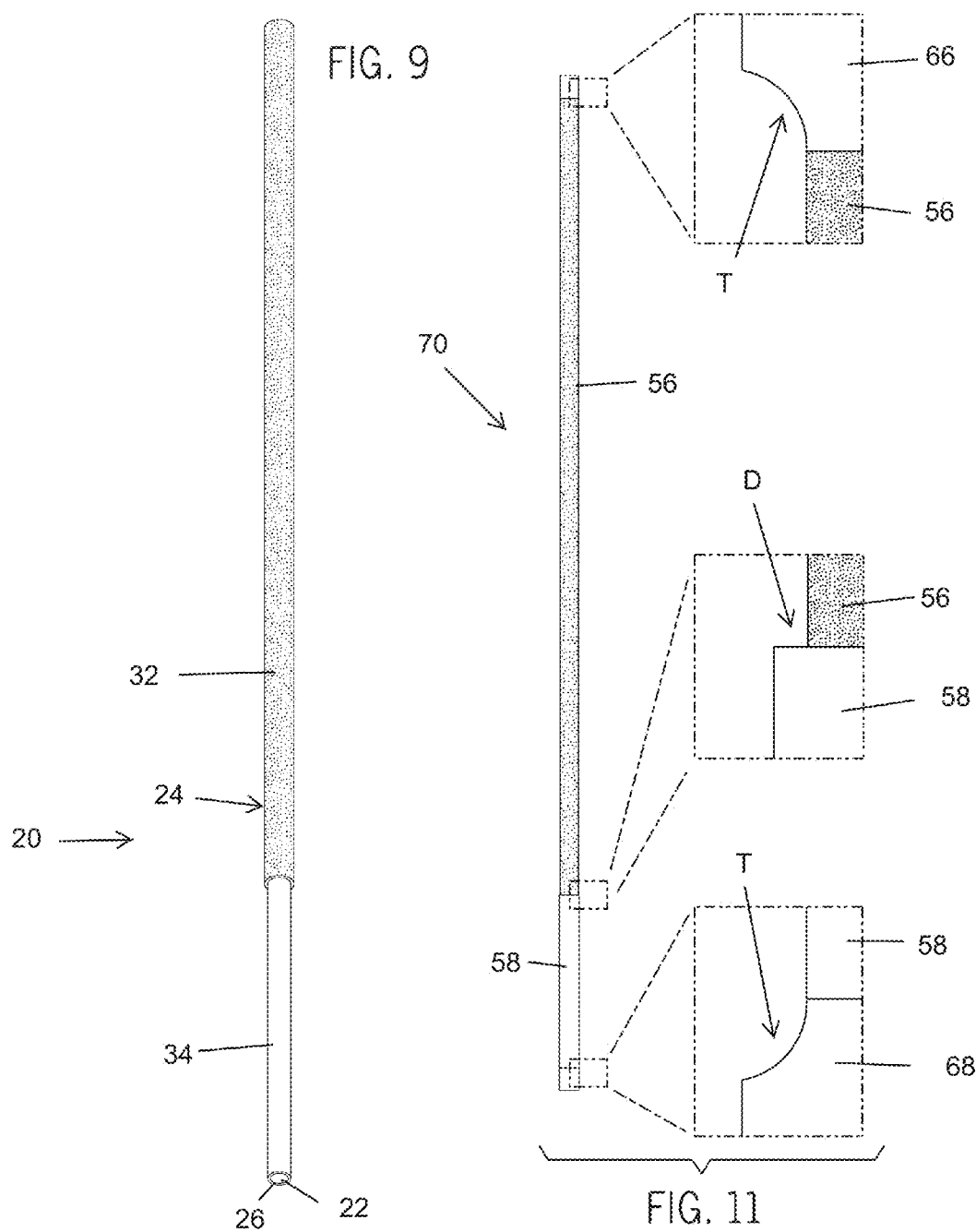

FIG. 9 shows a perspective view of an example wire of a lead according to the invention.

Figure 10:
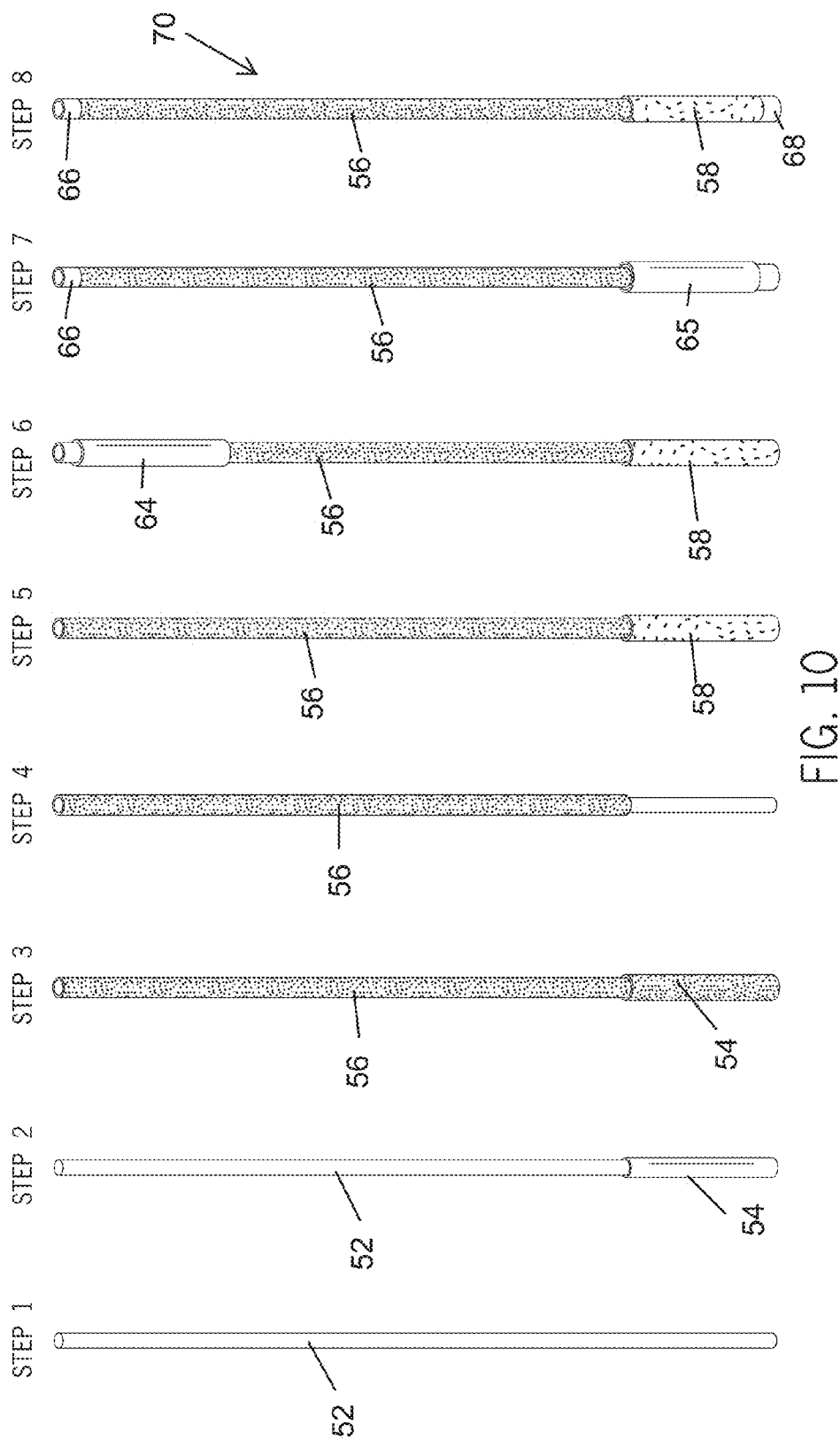

FIG. 10 shows steps in an example method for forming an RTS wire that may be used in a lead according to the invention.

FIG. 11 shows a side view with detailed sections in dashed lines of an RTS wire made using the steps of FIG. 10.

Figure 12:
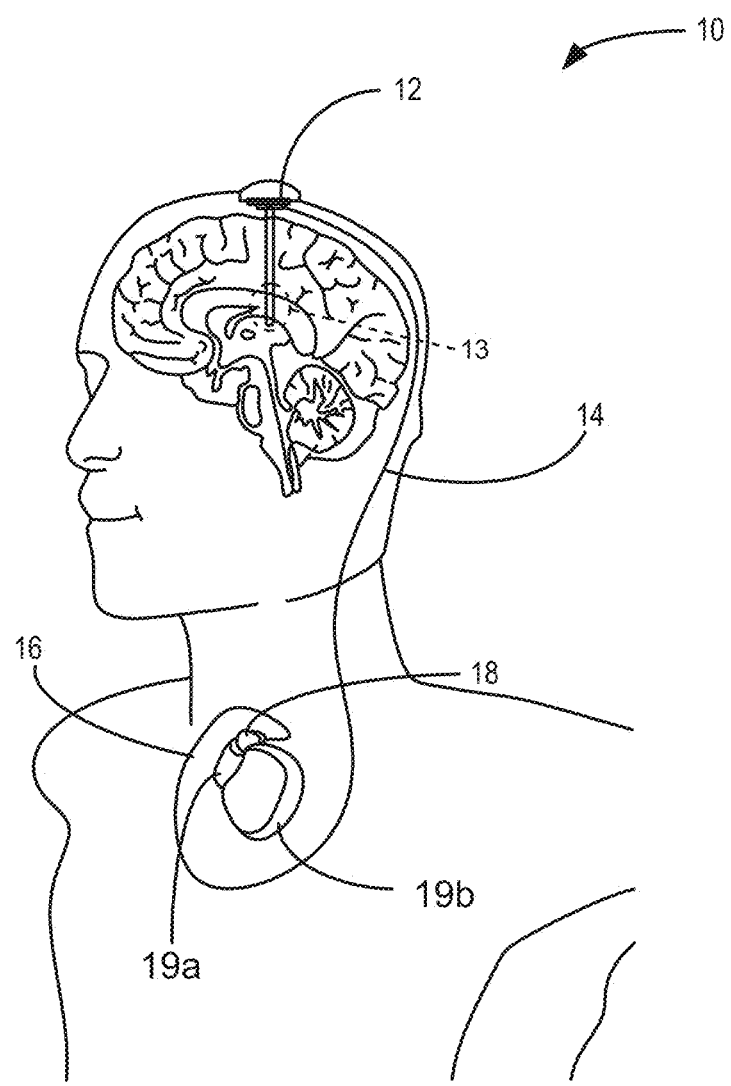

FIG. 12 illustrates a schematic of a deep brain stimulation system implanted in a patient.

Figure 13:
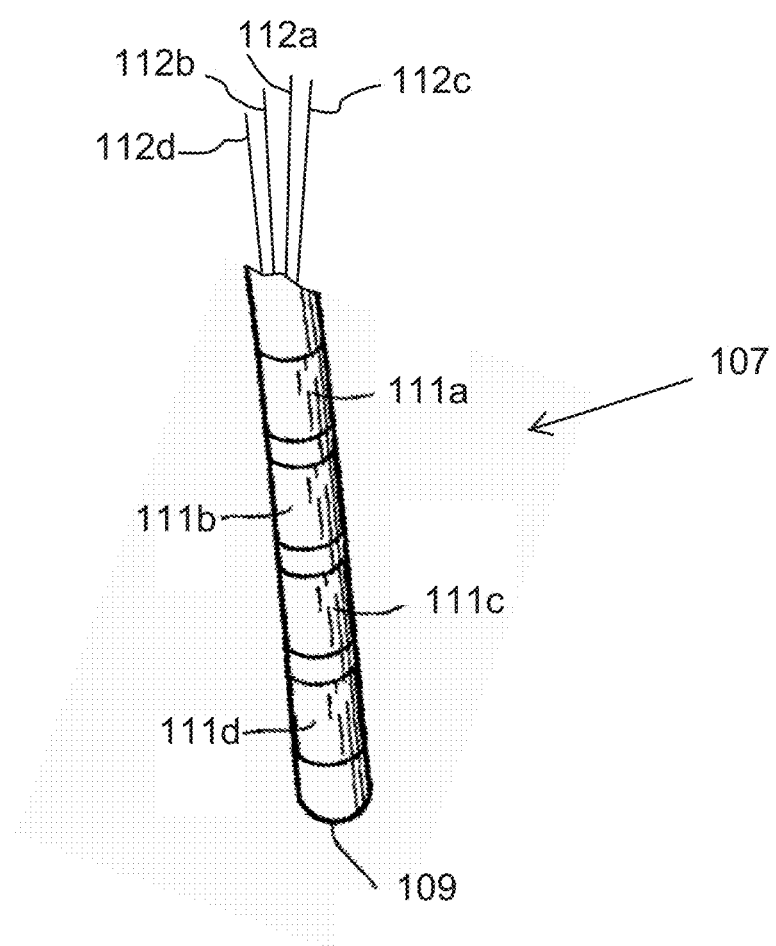

FIG. 13 is a partial perspective view taken along line 13 of FIG. 12 showing the distal end section of a lead.

Like reference numerals will be used to refer to like parts from Figure to Figure in the following description of the drawings.

DETAILED DESCRIPTION OF THE INVENTION

As outlined above, both electromagnetic simulations in human head models with implants and case studies have shown that traditional leads implanted in the brain can produce local heating during magnetic resonance imaging.

To overcome the problems with existing leads, in this disclosure, we present new neural prosthetic leads that can be used as MR-conditional intracranial implants in human subjects. These leads, which may be used in DBS systems or the like, are based on resistive tapered striplines (RTS) technology. The RTS-type lead design reduces the RF-induced currents along the DBS implant as well as the related increase of RF power deposition and potential tissue heating near the tip of the leads. As used herein, the improved leads may be referred to, for example, as "RTS leads", "DBS leads", or simply "leads". In the instance in which the improved leads are being compared to conventional leads, or are being prototyped, it will be so indicated by the context of the detailed description.

Similarly, the disclosed design incorporates an RTS design with abrupt variation of conductivity along its length, which essentially breaks up the energy of the RF wave in the wire by scattering. The nature of this product is to create a conductive, MRI compatible lead including the RTS design. The purpose and operation of this RTS design is to replace current metallic wires, which are not MRI compatible, in active implantable devices such that patients with these implants can undergo standard diagnostic medical care (e.g., MRI). A wire of the present disclosure may replace wires within the leads of an active implantable device. A lead typically constitutes an insulated tubing that has surface electrodes exposed at each end of the lead (one end of electrodes is exposed in the human body and either delivers or senses something, while the other end connects to a larger device that contains the electronics and battery of the implant). Wires inside the tubing and running the length of the tubing connect the electrodes on each end. These wires in conventional leads would be replaced with RTS wires of the present disclosure.

In one aspect, the present disclosure describes a prototype made of thin layered conductive ink on a polymer that when layered with different thicknesses can scatter radio frequency, thus making the prototype MRI compatible. The practical feasibility of the design was evaluated with preliminary studies (i.e., electromagnetic numerical simulations and temperature measurements). Electromagnetic numerical simulations based on finite elements suggested the possibility of over-30-fold reduction in energy absorption in the tissue surrounding the lead, when compared to traditional technology. Temperature measurements with a 3T MRI system, taken to address one of the main concerns regarding MRI examinations in patients with DBS implants, possible radio frequency (RF) heating, showed that the heating near the electrode of the prototype lead was less than 2 degrees Celsius. The findings from these preliminary studies suggest that our technology may be able to directly replace currently marketed commercial leads. Based on this characterization work, we learned that the best effect of reducing heating/power during MRI is achieved when the conductive layer is very thin. Thus, the next step of this prototype design was to translate the thin layer design into a form (e.g., substantially cylindrical wire) that can be easily incorporated and used in an implantable device. This led to the conception and development of thin film deposition (using either vapor deposition techniques or sputtering) onto single core polymer fibers.

Our novel MR conditional lead is based on resistive tapered stripline (RTS) technology, an innovative high-resistance technology designed to allow for decreased Specific Absorption Rate (SAR) and reduced artifacts of the MRI data while maintaining low lead resistivity for continuous current injection. Based on the knowledge that tapered dielectric structures can break up or scatter RF energy due to their unique frequency response characteristics, the lead wire is designed as a two-section stripline-based lead wire that provides an abrupt variation of electrical conductivity along its length. Contrary to a standard electrically homogeneous cylindrical wire, this RTS design can break up the induced current along the lead caused by the MRI RF coil. Subsequently, RF induced current along the RTS lead is less homogeneously distributed resulting in reduced energy deposited at the distal electrode.

The present disclosure provides a lead for an implanted medical device in which the lead is adapted for electrical communication with an electrical signal source and has a distal tip with an electrode. The lead comprises a wire adapted to be placed in electrical communication with electrode. The wire includes: (i) a core comprising a polymeric material, and (ii) a metallic layer surrounding an outer surface of the core. The metallic layer includes a first section having a first thickness and a second section having a second thickness, wherein the first thickness is greater than the second thickness. The lead is substantially transparent to radio frequency waves in clinically-applicable magnetic resonance environments to reduce radio frequency absorption and avoid substantial heating effects.

The metallic layer may comprise a metallic material selected from the group consisting of gold, titanium, platinum, cobalt-chromium alloys, cobalt, stainless steel, and mixtures thereof. The metallic layer may comprise a first metallic layer that contacts the core and a second metallic layer disposed on the first metallic layer. The second metallic layer may have a third section having a third thickness and a fourth section having a fourth thickness, wherein the third thickness is greater than the fourth thickness. The first metallic layer may comprise a metallic material selected from the group consisting of gold, titanium, platinum, cobalt-chromium alloys, cobalt, and stainless steel, and the second metallic layer may comprise a metallic material selected from the group consisting of gold, titanium, platinum, cobalt-chromium alloys, cobalt, and stainless steel.

A thickness of the first metallic layer may be in a range of 50 to 500 nanometers, or 50 to 400 nanometers, or 50 to 300 nanometers, or 50 to 200 nanometers, or 50 to 150 nanometers, or 60 to 140 nanometers, or 70 to 130 nanometers, or 80 to 120 nanometers. The third thickness of the third section of the second metallic layer may be in a range of 200 to 1500 nanometers, or 300 to 1400 nanometers, or 500 to 1300 nanometers, or 600 to 1200 nanometers, or 800 to 1000 nanometers. The fourth thickness of the fourth section of the second metallic layer may be in a range of 100 to 1000 nanometers, or 150 to 900 nanometers, or 200 to 800 nanometers, or 300 to 700 nanometers, or 400 to 600 nanometers. The core may be cylindrical, and may have a diameter in a range of 10 to 500 microns, or 20 to 400 microns, or 30 to 300 microns, or 40 to 200 microns, or 50 to 150 microns, or 60 to 100 microns.

The polymeric material comprising the core may be selected from the group consisting of nylons, polyesters, polyolefins, fluoropolymers, polyurethanes, and polyaryletherketones. A non-absorbable polymeric material (i.e., a polymeric material that does not degrade by biological mechanisms when implanted in a human) is preferred. Non-limiting example nylons include nylon 6-(poly(hexano-6-lactam), and nylon 66-(poly[imino(1,6-dioxohexamethylene) iminohexamethylene]). Non-limiting example polyesters include poly(ethylene terephthalate). Non-limiting example polyolefins include polyethylene and polypropylene. Non-limiting example fluoropolymers include polytetrafluoroethylene (PTFE), polyvinylidene difluoride (PVDF), and blends of polyvinylidene fluoride and polyvinylidene fluoride-co-hexafluoropropylene). Non-limiting example polyaryletherketones include polyether ether ketone (PEEK). The core may consist essentially of the polymeric material in that it does not include filler materials. Preferably, the polymeric material has a melting point above 200° C., or above 250° C., or above 300° C.

A terminal may be located at the distal tip of the wire for attachment to an electrode, and a terminal may be located at the proximal tip of the lead for attachment to an electrical signal source. The terminal may have a tapered inner surface and/or a tapered outer surface. The terminal may comprise a conductive metallic material such as gold, silver, copper, titanium, platinum iridium, and platinum.

The present disclosure also provides a lead for an implanted medical device in which the lead is adapted for electrical communication with an electrical signal source and has a distal tip with an electrode. The lead comprises a wire adapted to be placed in electrical communication with electrode. The wire includes: (i) a core comprising a polymeric material, and a metallic layer surrounding an outer surface of the core, wherein the metallic layer includes a discontinuity in electrical conductivity along its axial length. The lead is substantially transparent to radio frequency waves in clinically-applicable magnetic resonance environments to reduce radio frequency absorption and avoid substantial heating effects. When the lead is implanted in a patient and subjected to radio frequency waves in an magnetic resonance imaging device, the lead does not heat more than 2 degrees Celsius in an applied field of 3 Tesla.

The metallic layer has a first section having a first thickness and a second section having a second thickness, wherein the first thickness is greater than the second thickness. The polymeric material may be selected from the group consisting of nylons, polyesters, polyolefins, fluoropolymers, polyurethanes, and polyaryletherketones, and the metallic layer may comprise a metallic material selected from the group consisting of gold, titanium, platinum, cobalt-chromium alloys, cobalt, and stainless steel, and mixtures thereof. The first thickness may be in a range of 200 to 2000 nanometers, the second thickness may be in a range of 100 to 1900 nanometers, and the core may be cylindrical and have a diameter in a range of 10 to 500 microns. The first thickness and the second thickness create a step discontinuity in thickness in the metallic layer.

A terminal may be located at the distal tip of the wire for attachment to an electrode, and a terminal may be located at the proximal tip of the wire for attachment to an electrical signal source. The terminal may have a tapered inner surface and/or a tapered outer surface. The lead may further comprise an insulating outer coating. Non-limiting example materials for the insulating outer coating include polyurethane and polyp-xylylene) polymers (e.g., Parylene). The lead may comprise a bundle of the wires, in which each wire has an insulating outer coating, and wherein the multiple wires are packaged together in a single lead.

The present disclosure also provides an implantable medical device comprising an electrical signal source, an electrode, and a lead of the present disclosure. The wire places the electrical signal source and the electrode in electrical communication with one another. The implantable medical device may be selected from deep brain stimulation systems, cardioverter defibrillators, pacemakers, and spinal cord stimulators. The implantable medical device may be a deep brain stimulation system.

In one specific non-limiting embodiment, a lead of the present disclosure includes an RTS design including a polymer monofilament cylindrical fiber coated with gold (Au) and titanium (Ti), using two different coating thicknesses and lengths, respectively layer 1 and layer 2. Both materials have proven biocompatibility, along with strong adherence to one another and to nylon. However, other metallic materials can be used (e.g., platinum, cobalt-chromium alloys, cobalt, stainless steel, etc.) as long as they are biocompatible, conductive and can adhere to polymers. The length of each coated section (i.e., layer) and the thickness of the Au/Ti coating will depend on the final conductivity ratio desired, as this effects the amount of energy and, therefore, the amount of heat at the distal electrode. Non-absorbable monofilament sutures were chosen as the substrate for the RTS fibers given their biocompatibility, tensile strength and other mechanical properties. An example polymer could be a long-chain aliphatic polymer such as Nylon 6 and Nylon 6.6. This material has a high melting point, a property that is useful when coating the fibers, biocompatibility that has been shown to generate little tissue reaction, and a long history of use as a permanent implantable material.

Turning now to FIG. 9, there is shown an example wire 20 that can be used in a lead of the invention. The wire 20 includes a core 22, an outer metallic layer 24, and an inner metallic layer represented by line 26 in FIG. 9. An insulating coating (not shown) can cover the outer metallic layer 24. The outer metallic layer 24 in the non-limiting embodiment of FIG. 9 can comprise two sections of gold, that is, a top trace 32 of gold (high purity: 99.999%) which has a resistance of <20$\Omega$, and a bottom trace 34 of gold (high purity: 99.999%) which has a resistance of 400$\Omega$ ($\pm$10%). The top trace 32 of <20$\Omega$ overall resistance can be a gold sputtering layer and the bottom trace 34 of 400$\Omega$ total resistance can be a gold sputtering layer, with as sharp transition as possible between the two traces 32, 34. The inner metallic layer 26 can be a titanium (high purity: 99.999%) sputtering layer. In the non-limiting embodiment of FIG. 9, the core 22 comprises a nylon 6 suture having a diameter of about 70-80 microns, and is commercially available as the Ethilon® 6-0 non-absorbable suture.

FIG. 10 illustrates steps in an example process of layering different metallic materials (i.e., covering certain portions to layer different thicknesses). The process of FIG. 10 can be used to produce wires similar to wire 20 of FIG. 9.

In Step 1 of FIG. 10, a polymeric core is coated with a titanium layer 52 (e.g., 100 nanometers) to improve bonding between gold and the polymeric core. In Step 2, a mask 54 in the form of a tubular sleeve is placed over an end of the titanium coated polymeric core. Preferably, all masks are tight with no gaps to create the steepest edge between layers. In Step 3, gold is layered over the titanium layer to form a gold coating 56 (e.g., 600 nanometers) of resistance of about 20 ohms. Subsequently, in Step 4, mask 54 is removed. In Step 5, gold is layered over the titanium layer to form a gold coating 58 (e.g., 1000 nanometers) of resistance of about 400 ohms. Preferably, the total resistance of the gold coating 56 and the gold coating 58 is less than 500 ohms.

In Step 6, a mask 64 in the form of a tubular sleeve is placed over an end of the metal coated polymeric core and a 1.5 millimeter platinum top ring terminal 66 is deposited on an end of the metal coated polymeric core. In Step 7, a mask 65 in the form of a tubular sleeve is placed over an end of the metal coated polymeric core and a 1.5 millimeter platinum bottom ring terminal 68 is deposited on an end of the metal coated polymeric core. Subsequently, in Step 8, the mask 65 is removed, resulting in wire 70. The two thickness levels for the gold coating 56 and the gold coating 58 can be selected in order for the two layers to match the conductivity prescribed by the simulations shown in FIG. 4.

Looking at FIG. 11, the top ring terminal 66 and the bottom ring terminal 68 are tapered (at T in FIG. 11) to provide mechanical strength to the ends of the wire 70 in order for the wire 70 to be able to connect to electrodes that are connected to the wire 70. FIG. 11 also shows the step discontinuity D in which there is a sharp step height between two layers 56, 58 of different thickness.

There are numerous variations in coating thicknesses and materials that can be used in a wire of a lead of the invention. For example, in FIG. 11, the wire 70 has a first section of metallic coating surrounding the polymeric core and extending from the terminal 66 to the interface between coating 56 and coating 58, and a second section of metallic coating surrounding the polymeric core and extending from the terminal 68 to the interface between coating 56 and coating 58. The first section includes a titanium layer and a gold layer, and the second section includes a titanium layer and a gold layer. The titanium layer is the same thickness in both sections and the difference in thickness in the first section and the second section arises from a third section of gold and a fourth section of gold of different thicknesses. However, the first section and the second section may only include a single metallic material of different thicknesses in the first and second sections. Also, three or more sections of metallic material of different thicknesses may be used, with each section including one metallic material or two or more different metallic materials. The transition between sections of different thicknesses creates the step discontinuity in electrical conductivity in the wire.

Thus, some advantages and features of embodiments of the invention include: (1) MRI compatibility, (2) reduced RF-induced heating, (3) thin film deposition on a single polymer fiber, (4) multi-thickness layered deposition for RF scattering, (5) tapered terminal design for mechanical strength to allow for solid connections to electrode contacts, and (6) all materials are biocompatible and implantable (long-term use).

Any active implanted medical device that needs a conductive lead (e.g., cardioverter-defibrillators, guidewires, pacemakers, spinal cord stimulators, and deep brain stimulation systems) can instead incorporate and utilize a lead of the present disclosure in order for the lead of these devices to now become MRI compatible (providing hundreds of thousands of patients standard medical care that was previously unavailable to them).

The DBS leads are divided into segments with different unmatched impedances that allow reflecting back to the input parts of the incoming RF emitted from the MR transmit coil, thereby minimizing RF deposition into the patient. Conversely, the RTS-type structure reduces the low-frequency resistance (that is, the real part of the impedance) to preserve the battery life of the neurostimulator. The RTS-type structure of the leads allows for very low overall DC resistance of the leads using the novel materials and thus the novel DBS system will still have a standard battery life, which cannot be achieved using traditional purely resistive leads.

This improved lead design significantly impacts the neural prosthetics field by creating a new state-of-the-art lead for a medical implant that is compatible with a wider range of MRI use. As the disclosed leads achieve a high degree of RF-transparency, maintain the current DBS lead form factor, and containing only a minimal amount of metal, this allows for the scanning of patients even under very broad conditions, presently absolutely contraindicated. These conditions include: the use MRI in normal operating mode (whole-body SAR of 2 W/kg, whole-head SAR of 3.2 W/kg), the use of 3 T or higher static fields, the use of RF transmit body coil, and the use of multichannel transmit coils.

This allows patients with DBS implants to benefit from the complete diagnostic benefits of MRI, including for example disease diagnosis in body soft tissues. This will have a high-impact on public health because, while MRI and non-soft tissue CT examinations are ranked by physicians as the most important technologies affecting their ability to treat patients, currently less than 5% of the patients with DBS benefit from MRI, and even then only a partial MRI given the recited restrictions on use.

It is contemplated that besides the FDA approved applications of Parkinson's disease, dystonia, and obsessive compulsive disorder, the proposed leads implementing RTS technology may be employed in future clinical applications of DBS including major depressive disorder, disorder and epilepsy and potentially, with further testing, in other active implants such as cardiac pacemakers which are implanted in hundreds of thousands of patients worldwide.

Moreover, the disclosed leads may offer other benefits unrelated to their improved MRI compatibility. For, example, these leads may be less susceptible to electromagnetic interference (EMI) from external RF sources such as for example, metal detectors, anti-theft systems and communication systems (for example, cell phones, RF towers).

Referring particularly to FIG. 12, a DBS system 10 is illustrated including an insulated lead 14 having electrode probe 12 that is capable of both stimulating populations of neurons and measuring single-unit neuronal activity. The probe 12 is typically implanted in a targeted area, for example, the subthalamic nucleus, and electrodes of the probe are connected with the insulated lead 14 that is passed under the skin of the head, neck, and shoulder to a neurostimulator 16. The neurostimulator 16 typically sits inferior to the clavicle and is programmed to operate the DBS system 10. A pulse generator 18, a controller 19a, and battery pack 19b that powers the apparatus are all included in the neurostimulator 16.

Still referring to FIG. 12, in operation, the DBS system 10 acquires neuronal activity, or spike train, data with the electrode probe 12. This neuronal activity data is carried via the lead 14 to the neurostimulator 16 where it is processed by the controller 19a. The controller 19a analyzes this data and predicts a responsive stimulation signal that will prevent future pathological neural events. The stimulation signal is generated by the pulse generator 18 and delivered via the lead 14 to the electrode probe 12, which administers the stimulation signal to the targeted area. It is contemplated that the response may inhibit the neuron, excite the neuron, or do nothing.

Looking now at FIG. 13, there is shown a distal end section 107 of the electrode probe 12 of the lead 14. The distal tip 109 of the lead 14 includes ring electrodes 111a, 111b, 111c, 111d that are each connected to wires 112a, 112b, 112c, 112d respectively. The wires 112a, 112b, 112c, 112d may each be wires 70 of the invention. The wires 112a, 112b, 112c, 112d may comprise a bundle.

The disclosed wire structure of this specification creates abrupt differences in conductivity over the length of the lead, which breaks up the energy of the radio frequency waves in the lead wire by scattering. By virtue of this structure, radio frequency induced currents in the lead structure is largely avoided which prevents heating of the lead at the ends which could result in soft tissue heating damage. The lead is substantially transparent to radio frequency waves in clinically-applicable magnetic resonance environments to avoid radio frequency heating effects. Presently, clinically-applicable magnetic resonance environments use MRI systems with a main magnetic field strength of 7 T or less. MRI systems using 3 T, or 1.5 T, or 1 T or 0.5 T are also common. The Larmor frequency of the nuclear spin species being imaged is related to the main magnetic field strength of the MRI scanner. At higher field strengths, the Larmor frequency increases, and thus the potential for undesirable heating effects will similarly increase.

The present disclosure provides a novel technology to allow the safe use of MRI in patients with DBS implants. The safety evaluation of the RF-induced heating injury risks in patients with implanted medical devices undergoing MRI is based on several testing strategies and tools, including pre-clinical (experimental, computational, and animal testing) as well as clinical testing. Experimental testing includes measuring temperature changes near the device while it is implanted in a gel that simulates the electrical and thermal characteristics of the human body [Ref. 23]. Additionally, computational modeling has been increasingly used to complement experimental testing, as it allows for extensive, cost-effective and systematic analysis of several variables that can influence the amount of current flow into an implant and the amount of energy absorbed by surrounding tissue.

Several proposals have been made to modify the design of the implant to solve the issue of RF-induced heating without interfering with device performance, such as introducing RF chokes [Ref. 24], modifying the materials of the lead (e.g., carbon-loaded leads) [Ref. 25-30], or coiling the wire [Ref. 31]. A new type of lead based on "resistive tapered stripline" (RTS) technology [Ref. 32] is herein described. The RTS design can be best understood by recalling oceanic science, where an area of study is the prevention of destructive standing waves (clapotis) [Ref. 33]. Special constructions reinforced with wide, rubble-mound beams break up wave energy over some distance, preventing the formation of clapotis. Similarly, tapered dielectric structures can break up or scatter RF energy due to their unique frequency response characteristics. This characteristic has been studied for many applications including microwave, millimeter-wave and optical-wave engineering [Ref. 34-36], as well as stealth aircraft technology [Ref. 37]. Among other things, this present disclosure presents a two-section stripline-based design (FIG. 1a) with an abrupt transition of electrical conductivity along its length. Contrary to a common metallic wire, this design can break up the induced RF current along the lead (FIG. 1b) caused by the MRI RF coil. Consequently, RF-induced current along the RTS lead is more heterogeneously distributed and significantly reduced at the electrode (FIG. 1c).

Theoretical Background on RTS Design.

Resistively tapered Vee dipole antennas were first successfully introduced in landmine detection [Ref. S1]. The design consisted of a linearly tapered thin film deposit, which allowed a radiation profile less affected by the ground properties. When the conductivity is tapered from the feed point to the extremity according to the Wu-King (WK) resistive profile [Ref. S2], the antenna field radiation pattern uniformity from the feed point to the open end is greatly improved. Numerical electromagnetic (EM) simulations validated experimentally were successfully used in evaluating voltage differences within a 20% accuracy for an RTS design of thin triangular-shaped conductive sheets attached to a feeding transmission line by thin perfect electric conductor (PEC) traces [Ref. S3]. In contrast with all previously proposed RTS designs, including the WK profile, which aimed to improve the antenna performance, the design proposed in this disclosure decreases the antenna performance and the induced currents along the wire. The RTS implant exposed to an RF field can be represented with a hybrid model composed of an antenna attached to a transmission line, which consists of resistive traces with sharp changes in conductivity to maximize reflections, followed by a load such as an electrode connected to the tissue (see FIG. 1a). As described in Ref. S4, the equivalent antenna (i.e., the entire RTS lead) receives the electromagnetic field and injects it into the first port (i.e., layer) with impedance $Z_1$ of such a network (see FIG. 1b). A portion of the power transmitted to the first port of the RTS is reflected back as a result of an impedance mismatch between the first port and the antenna, while a remaining portion is supplied to the second layer of the RTS. The impedance of this second port is intentionally mismatched to reflect the greatest amount of power back to the implantable pulse generator (IPG) and away from the electrode that is in contact with the tissue. The fractional power reflected away and delivered to the tissue can be computed from the reflection $\Gamma_2^R$ and transmission $\Gamma_2^T$ coefficients:

$$\Gamma_0^R = \frac{Z_1 - Z_0}{Z_1 + Z_0} \quad \Gamma_0^T = \frac{2Z_1}{Z_1 + Z_0}$$

$$\Gamma_1^R = \frac{Z_2 - Z_1}{Z_2 + Z_1} \quad \Gamma_1^T = \frac{2Z_2}{Z_2 + Z_1}$$

$$\Gamma_0^R = \frac{Z_1 - Z_0}{Z_1 + Z_0} \quad \Gamma_2^T = \frac{2Z_L}{Z_L + Z_2}$$

(S1)

One must consider the superposition of two steady state sine waves in the RTS traveling in opposite directions (see FIG. 1b): one forward towards the tissue/electrode (blue) and one backward (red) reflected by the mismatched boundary towards the IPG. The first and second layer of the RTS act both as an antenna and transmission line for the signal that is reflected back away from the tissue/electrode. The overall signal $\Phi$ present in the electrode, which is the result of the superposition of all the direct and reflected back signals towards the first layer, is [Ref. S4]:

$$\Phi = \Delta H_{OZ1}\sigma_1 L_1 + \Delta H_{OZ2}\sigma_2 L_2 - (\Gamma_0^R + \Gamma_1^R) \\ -e^{-4(L_1\lambda_1 + L_2\lambda_2 + L\lambda_L)}(\Gamma_1^R e^{2(L_1\lambda_1 + 2L_2\lambda_2 + 2L\lambda_L)} + \\ \Gamma_2^R e^{2(L_1\lambda_1 + L_2\lambda_2 + 2L\lambda_L)} + \Gamma_2^R e^{2(2L_1\lambda_1 + L_2\lambda_2 + 2L\lambda_L)} - \\ \lambda_L^2 e^{-4L_1}(\Gamma_0^R + \Gamma_1^R) - \lambda_L^2(\Gamma_0^R + \Gamma_1^R + \Gamma_2^R)) - \Gamma_L^R \\ (e^{-2(L_1\lambda_1 + L_2\lambda_2 + L\lambda_L)} - \lambda_L^2 e^{-2(2L_1\lambda_1 + L_2\lambda_2 + L\lambda_L)})$$

(S2)

where $\lambda_i$ is the propagation coefficient, $L_1$ and $L_2$ are the lengths of the first and second layer, respectively, $\Delta H_{OZ1}\sigma_1 L_1$ is the signal received by the first layer of the RTS, and $\Delta H_{OZ2}\sigma_2 L_2$ is the signal received by the second layer. The signal $\Phi$ that emerges from the left side of the port is the sum of all the terms that represent the intrinsic reflections in the RTS. The terms $\Delta H_{OZ1}$, $\Delta H_{OZ2}$ (i.e., the variation of the magnetic field along the RTS or z-direction in the two adjacent Yee cells), and $\lambda_i$ can be estimated using a numerical approach, such as the finite element method (FEM) algorithm used herein, based on the particular geometrical model considered [Ref. S5].

Equation (S2) has four positive definite unknowns, i.e., $\sigma_1$, $\sigma_2$, $L_1$, $L_2$. Furthermore, there are two additional minimization constraints on the upper limit ($\sigma_T$) of the desired overall RTS resistance and total RTS length:

$$0 > \sigma_1 + \sigma_2 \geq \sigma_T L_1 + L_2 = L$$

(S3)

Equation (S2) has been introduced only to give an insight into the theory of RTS design. The following section presents a more detailed description of the fields inside the RTS leads.

The peak inductance of the lead can be estimated as follows:

$$L_{MAX} = \mu \frac{\iiint_x \|H(x,y,z)\|^2 dx dy dz}{\left(\iint_{\delta_{1,2}} J(x,y,z) \cdot k(x,y,z) dS\right)^2}$$

(S4)

where $|H(x,y,z)|$ is the complex magnitude of the Fourier transform or harmonic component of the magnetic field at the Larmor frequency $f_0 = 128$ MHz, $\mu$ is the permeability of the material (see Table S1), R is the domain composed of RTS wire and insulation, $\Theta_{1,2}$ is the section, k is the unitary vector between layers 1 and 2 of the RTS, and $J(x,y,z)$ is the current density inside the lead. One can only estimate $L_{MAX}$ or the peak inductance of an ideal inductor which is an ideal magnetic field generator that stores the magnetic field energy generated by the supplied current, whereas in a real inductor the inductance L is always lower than $L_{MAX}$ because of magnetic flux losses.

The main or static magnetic field $B_0$ present in an MRI will produce a spin or precession of nuclei of the hydrogen atoms (protons) in the water molecules in the tissue. The precessional path of these protons around the magnetic field is circular like and sometimes described in terms of a spinning top. The Larmor or precessional frequency in MRI refers to the rate of precession of the magnetic moment of the proton around the external magnetic field and is related to the strength of the magnetic field $B_0$. The frequency of all fields considered here is the Larmor frequency (i.e., 128 MHz at 3 T). The behavior of a RTS wire inside an electromagnetic field can be studied as a linear antenna under the thin wire assumption (i.e., the diameter d of the geometry is d<λ/100, i.e. d=100 μm). For an ideal linear thin antenna the current density J(x,y,z) which determines the fundamental fields H(x,y,z) and E(x,y,z) is [Ref. S6]:

$$J(x,y,z)=kI(z)\delta(x)\delta(y) \quad (S5)$$

where k and I(z) are the unit vector and current intensity along the implant along the z-axis, as shown in FIG. 1c. The current density field can be found by solving the following Pocklington's integral equation [Ref. S7]:

$$\int_{-L/2}^{L/2} I(z)\left(\frac{\partial^2}{\partial z^2} + k^2\right)G(z-z')\,dz' = -j\omega\varepsilon_w(z)\|E_{B_1}(z)\| + I(z)\frac{j\omega s_w}{\sigma_w(z)} \quad (S6)$$

where $E_{B1}(z)$ is the electric field on the surface of the wire induced by the $B_1$ field, the constant k=2π/λ is the free space wave number, $\varepsilon_w(z)$ and $\sigma_w(z)$ are the electrical permittivity and conductivity, respectively, along the wire, and G(z) is Green's function. Note that equation (S6) also includes the conductivity profile of the wire, which is not typically present in implanted wires due to the common assumption of an ideal conductor. The kernel that approximates the exact Green's function of the integral in equation (S6) is given the following [Ref. S6]

$$G(z-z') = \frac{e^{-jkR}}{R} \cdot R = \sqrt{(z-z')^2 + \frac{d^2}{4}} \quad (S7)$$

In the case of the RTS geometry, equation (S6) becomes:

$$\int_0^{L_2} I(z)\left(\frac{\partial^2}{\partial z^2} + k^2\right)\frac{e^{-jkR}}{R}dz' + \int_{L_2}^{L_1+L_2} I(z)\left(\frac{\partial^2}{\partial z^2} + k^2\right)\frac{e^{-jkR}}{R}dz' = \\ -j\omega\varepsilon_w(z)\left(\|E_{B_1}(z)\| - \frac{I(z)}{L_w(z)\sigma_w(z)}\right) \quad (S8)$$

where $\sigma_w(z)$, $\varepsilon_w(z)$ and $L_w(z)$ are respectively equal to $\sigma_1$, $\varepsilon_1$, and $L_1$ when $L_2 \geq z \geq L_1+L_2$ and equal to $\sigma_2$, $\varepsilon_2$, and $L_2$ when $z<L_2$.

The following current distribution along the wire is an approximate solution of equation (S8):

$$I(z) = \begin{cases} I_2\sin(k(L_1+L_2-z)) & L_2 \geq z \geq L_1+L_2 \\ I_1 kz & z < L_2 \end{cases} \quad (S9)$$

Equation (S9) is the typical shape of the ideal current distribution in an RTS wire as sketched in FIG. 1c. A more precise current distribution estimated using EM numerical simulations is shown in FIG. 2d. The RTS design reduces the overall inductance of the lead (FIG. 2c). Additionally, the current density has a minimum value along the lead in proximity to the electrode (FIG. 2d), thereby reducing the risk for energy absorption in the surrounding tissue.

Finally, the skin depth $\delta_s$ plays an important role in the RTS design:

$$\delta_s = \sqrt{\frac{2}{\sigma\mu\omega}} \quad (S10)$$

where $\omega=2\pi f=2\pi 128\times 10^6$ Hz, $\mu=4\pi\cdot 10^{-7}$ H/m and $\sigma_1=1.968\times 10^6$ S/m and $\sigma_2=25.61\times 10^3$ S/m are the conductivity of the two RTS layers, respectively, calculated by the simulations. Note that for these values, the skin depth of the optimal RTS design was 31.63 μm for the first layer and 278 μm for the second layer, which is higher than the thickness of the modeled lead, which was 9.7 μm. The FEM simulation results shown in FIG. 2 take in consideration the skin depth effect.

Further background on RTS design can be found in U.S. patent application Ser. No. 14/279,540, filed May 16, 2014, which is incorporated herein by reference for all purposes as if set forth in its entirety herein.

Overall, different non-limiting example RTS designs were used for the study of Example 1 below: (a) an initial design constructed with conductive ink deposited on a polymer substrate ("flat-design"), and (b) a second wire-based design ("wire-design"). The flat-design was used for the simulations in phantom (FIGS. 1 and 2), the manufacturing of the first non-limiting example prototype, and the bench testing experiments (FIG. 3). The wire-design was used for simulations with human body models (FIG. 4) and manufacturing of a second non-limiting example prototype (FIG. 5). Both simulations and measurements confirmed that the RTS design "cloaks" the incident RF-field [Ref. 38], so that the lead is "RF-transparent" (i.e., the presence of the lead does not significantly affect the RF fields present in a phantom).

The invention is further illustrated in the following Example which is presented for purposes of illustration and not of limitation.

Example 1

Methods

Theoretical background on RTS design. The RTS implant exposed to an RF field can be represented with a hybrid model composed of an antenna attached to a transmission line, which consists of resistive traces with sharp changes in conductivity to maximize reflections, followed by a load such as an electrode connected to the tissue (see FIG. 1a). As described in Ref. 32, the equivalent antenna (i.e., the entire RTS lead) receives the electromagnetic (EM) field and injects it into the first port (i.e., layer) with impedance $Z_1$ of such a network (see FIG. 1b). A portion of the power transmitted to the first port of the RTS is reflected back as a result of an impedance mismatch between the first port and the antenna, while a remaining portion is supplied to the second layer of the RTS. The impedance of this second port is intentionally mismatched to reflect the greatest amount of power back to the implantable pulse generator (IPG) and away from the electrode that is in contact with the tissue. The fractional power reflected away and delivered to the tissue can be computed from the reflection $\Gamma_2^R$ and transmission $\Gamma_2^T$ coefficients:

$$\Gamma_0^R = \frac{Z_1 - Z_0}{Z_1 + Z_0} \quad \Gamma_0^T = \frac{2Z_1}{Z_1 + Z_0}$$
$$\Gamma_1^R = \frac{Z_2 - Z_1}{Z_2 + Z_1} \quad \Gamma_1^T = \frac{2Z_2}{Z_2 + Z_1} \quad (1)$$
$$\Gamma_0^R = \frac{Z_1 - Z_0}{Z_1 + Z_0} \quad \Gamma_2^T = \frac{2Z_L}{Z_L + Z_2}$$

One must consider the superposition of two steady state sine waves in the RTS traveling in opposite directions (see FIG. 1b): one forward towards the tissue/electrode (blue) and one backward (red) reflected by the mismatched boundary towards the IPG. The first and second layer of the RTS act both as an antenna and transmission line for the signal that is reflected back away from the tissue/electrode. The following equation is the typical shape of the ideal current distribution in an RTS wire as sketched in FIG. 1c:

$$I(z) = \begin{cases} I_2 \sin(k(L_2 - z)) & L_2 \geq z \geq L_1 + L_2 \\ I_1 kz & z < L_2 \end{cases} \quad (2)$$

where $L_1$ and $L_2$ are the lengths of the first and second layer. A more precise current distribution estimated using EM numerical simulations is shown in FIG. 2d. The RTS design reduces the overall inductance of the lead (see FIG. 2c). Additionally, the current density has a minimum value along the lead in proximity to the electrode (see FIG. 2d), thereby reducing the risk for energy absorption in the surrounding tissue.

Computational Modeling and Simulations

A computational model was used to evaluate several possible electrical and geometrical configurations of the RTS lead to minimize the absorption of energy and the temperature increase at the electrode. The model included a clinical 3 T MRI RF transmit coil, which operates at 128 MHz [Ref. 39], loaded with a gel-filled phantom and an implanted lead (see FIGS. 1d and 1f). The design contained discrete sections of variable conductivity and length, connected in series, with a fixed length (i.e., to yield a total length of 40 cm. to match common lead lengths for implantable devices [Ref. 13]) and a fixed resistance at low-frequency (i.e., 400Ω, i.e., less than the typical impedance in patients [Ref. 40]) (see FIG. 2a). Simulations were performed to determine the values of electrical conductivity (i.e., $\sigma_1$ and $\sigma_2$) and length (i.e., $L_1$ and $L_2$) for a two-section RTS design (see FIG. 3a and FIG. 4e) in order to build a prototype for experimental testing. The parameter used in the simulations to evaluate the power absorbed inside the phantom was the specific absorption rate (SAR) averaged over 10 g of tissue (10 g-avg. SAR). SAR (W/kg) is a measure of the energy rate absorbed by the human body when exposed to an RF field and it is the dosimetric parameter used in RF safety guidelines [Ref. 41]. SAR is averaged either over the entire body, or over 1 g or 10 g of tissue. Temperature simulations on the final optimized lead design were also performed.

Lead Design Optimization

All lead design optimization included models of a realistic MRI birdcage transmit coil tuned at the Larmor Frequency $f_0$=128 MHz, an ASTM phantom [Ref. S8, S9], a PtIr wire, and a realistic RTS lead that allowed for a physically realizable solution. The dimensions and material properties of the coil, lead, and phantom are listed in the Table S1. Detailed methods on the simulations can be found in [Ref. S10]. The computational models were created with the finite element methods (FEM) electromagnetic solver high frequency structure simulator (HFSS) v15.0 and circuit solver Designer v8.0, (ANSYS, Inc., Canonsburg, Pa.). The FEM method [Ref. S11] allowed for high geometrical modeling accuracy (i.e., minimal tetrahedral length equal to 45 μm) at the electrode, where the highest electric field was observed [Ref. S12, S13, S14]. The parameter used to evaluate numerically the energy deposition in the phantom was the specific absorption rate (SAR) averaged in a volume with a 10 g mass (10 g-avg. SAR) [Ref. S15]. SAR (W/kg) is a measure of the energy rate absorbed by the human body when exposed to a RF field and is the dosimetric parameter used in RF safety guidelines. For each lead design simulation, the 10 g-avg. SAR was computed in a location at 0.1 mm from the anterior face of the lead contact in the direction of the positive Z-axis. In order to obtain a high increase of 10 g-avg. SAR, the lead was placed in a volume with high tangential electric field magnitude [Ref. S16] (see FIG. 1e).

The flat-design RTS lead (FIG. 3a) contained two discrete sections of variable conductivity and length, connected in series. Three requirements were used to minimize the optimal design search including: (a) total length fixed to 40 cm to match common lead lengths for implantable devices [Ref. S17], (b) conductivity of the proximal section higher than the distal section; and (c) total low-frequency resistance of the lead equal to 400Ω, i.e., less than the typical impedance in patients [Ref. S18].

Additional numerical simulations were also performed in order to determine the best design parameters and estimate the performance of the wire-based RTS design since it utilizes different materials and geometry. A detailed view of this model can be seen in FIG. 4d. The model contains four identical RTS fibers each divided into six fixed-length sections of variable thickness which allow the model to simulate the effects of varying length (by making two or more adjacent sections equal in thickness) and number of sections (by choosing the number of changes in adjacent section thickness). Total lead resistance was still R=400Ω and the ratio of layer thicknesses $t_1/t_2$=20. The simulation showed that the optimal design was obtained by dividing the lead into two sections of equal lengths $L_1$=0.2 m and $L^2$=0.2 m and yielded a 33% reduction in peak 10 g-avg. SAR within 1 cm of the lead (see also FIG. 6 for electric field and magnetic field maps). A summary of optimal designs by number of sections can be seen in FIG. 4e.

Additional analysis on effect of lead design—Additional simulations were performed to evaluate the effect on 10 g-avg. SAR of different design variables, including: shape (i.e., wire vs. thin), lead conductivity, and proximal end boundary conditions (i.e., insulated vs. uninsulated). The results of the simulations are shown in FIG. 7. Notably, the simulations, manufacturing, and bench testing were performed with the electrode exposed only on a single side, although additional simulations included the case of two exposed ends. Higher SAR was predicted for models with wires compared to thin RTS geometries, in line with the skin depth calculations discussed in equation (S 10). Furthermore, based on the selected design the RTS leads showed lower SAR than leads with homogeneous conductivity (see also FIG. 2a, case $\sigma_1/\sigma_2=1$).

Temperature Simulations

The temperature simulations were performed by implementing the following heat equation in solids, which corresponds to the differential form of Fourier's law:

$$\rho C_p \frac{\partial T}{\partial t} = \nabla \cdot (k_T \nabla T) + \iiint_\phi \frac{\sigma \|B\|^2}{\rho} dxdydz \quad (S11)$$

where T [K] is the absolute temperature, $C_p$[J/(kg K)] is the specific heat capacity at one atmosphere of constant pressure, $\rho$[kg/m3] is the mass density, $k_T$ [W/(m K)] is the thermal conductivity (see Table S1 for values) and Ø is the volume of 10 g of polyacrylic acid (PAA) in the point where T is estimated. The temperature distribution values of T were estimated by solving the heat equation in solids (equation S11), which is used to model heat transfer by conduction only. The equation was solved considering as a heat source term the SAR calculated by the HFSS-based EM simulations (right term). The geometry consisted of two blocks modeling the ASTM phantom (410×80×590 mm$^3$ and 150×80×290 mm$^3$). The external surfaces of the ASTM phantom were set to Dirichlet boundary conditions with T=20.15° C. The solution was calculated in a Cartesian 3D coordinate system and consisted of temperature values T. The calculations were performed using a FEM-based commercially available software (Multiphysics 4.4, COMSOL, Burlington, Mass.).

Uncertainty Analysis

A simulation study to assess the uncertainty of design and simulation parameters was performed (see Table 1 below) following the approach used in Neufeld et al. [Ref. 42]. The parameters studied were selected such that they could be considered independent. To determine the impact of the contribution of an individual parameter to the total uncertainty of the simulations, first two simulations were run for each parameter by assigning two different values to each parameter studied. The first value was the one used for the simulations shown in FIG. 2 whereas the modified value was set to a realistic value that could occur due to either design choice or manufacturing tolerance. Assuming linear dependence of the measurement values on the varying parameter, a sensitivity factor was determined for each parameter by calculating the percent error difference between the two evaluation results and then dividing by the absolute value of the change in parameter value. The individual uncertainty contribution was then calculated by multiplying the sensitivity and the standard deviation of the parameter uncertainty. The standard deviations were small for parameters such as the implant length, which can be accurately determined, and large for parameters such as the conductivity.

The analysis confirmed a high sensitivity—and relative high uncertainty—to the thickness and dispersion properties of the insulation layer, in line with previous studies [Ref S8]. Lower SAR values resulted with a 25.4 μm vs. 50.8 μm dielectric thickness of both insulation and substrate, which is consistent with the notion that insulation characteristics strongly affect the antenna behavior [Ref. S12]. Moreover, FIG. 2a shows that the ideal length of layer 2 is 3.3 cm, thus microscopic surface mount resistors (e.g., 0.4×0.2×0.2 mm$^3$), often connected to each electrode in commercial EEG/fMRI caps, and cannot be used to create an ideal RTS geometry since they are too short. Additionally, larger resistors would be too bulky and rigid to be attached to a microscopic wire of an implant. Finally, the simulations showed that conductor thickness plays a fundamental role in the RF-induced currents [Ref. S19], with a low uncertainty coefficient. Notably, a homogenously conductive thin design decreased the current density at thicknesses less than the skin depth (See FIG. 7). The uncertainty analysis performed showed that the permittivity of the binder used in conductive inks can significantly affect 10 g-avg SAR. Binders [Ref. S20] serve to bind together the nanoparticles of the material, ensure the necessary viscosity for proper transfer of the ink from the press to the substrate, provide adhesion to the substrate, and contribute to the drying speed and resistance properties of the ink [Ref. S21]. The relative permittivity of binders varies from two to fifteen [Ref. S22] or higher in composites [Ref. S23], and it is essential for the RTS effect presented in this paper, as no RTS effect was found in simulations with binders with the unity relative permittivity of vacuum.

TABLE 1

Uncertainty analysis. The methods used were based on the work of Neufeldet al.[42]. To evaluate the uncertainty of the quantities of interest derived by the simulations (i.e., 10 g-avg. SAR or the magnitude of incident electric field "$E_{RTS}$") Two simulations were run for each parameter by assigning two different values ("Val 1" and "Val 2") to each parameter studied. The first value ("Val 1") was the one used for the simulations shown in FIG. 2, whereas the modified value ("Val 2") was set to a realistic value that could occur due to either design choice or manufacturing tolerance. The results obtained for each value ("Result 1" and "Result 2", respectively) were used to evaluate sensitivity factor of the quantity evaluated (10 g-avg. SAR or magnitude of incident electric field "$E_{RTS}$"). The standard deviation ("Std. Dev.") was derived from literature

| Parameter | Quantity | Val 1 | Val 2 | Result 1 | Result 2 | Sensitivity factor [%/mm] | Std. Dev | Uncertainly [%] |
|---|---|---|---|---|---|---|---|---|
| Contact Width [mm] | 10 g-avg. SAR or | 0.381 | 0.762 | 6.98 | 7.22 | 9.12% | 0.1 | 0.9% |
| Contact Length [mm] | electrode [W/kg] | 1.5 | 3.0 | 6.98 | 7.28 | 2.85% | 0.1 | 0.3% |
| Contact Thickness [mm] | | 0.0098 | 0.0196 | 6.98 | 7.00 | 32.6% | 0.1 | 3.3% |
| Substrate Thickness [mm] | | 0.0254 | 0.0508 | 6.98 | 6.9 | 43.9% | 0.1 | 4.4% |
| Insulation Thickness [mm] | | 0.0254 | 0.0508 | 6.98 | 7.07 | 52.0% | 0.1 | 5.2% |
| $\varepsilon_T$ (Substrate) | | 3.4 | 6.8 | 6.98 | 7.11 | 0.56% | 2.00 | 1.1% |
| $\varepsilon_T$ (Insulation) | | 2.5 | 5.0 | 6.98 | 7.00 | 0.13% | 2.00 | 0.3% |
| $\varepsilon_T$ (Ink Lead) | | 5.0 | 2.5 | 6.98 | 6.99 | 0.04% | 2.00 | 0.1% |
| $\sigma$(Contact) [S/m] | | $9.3 \cdot 10^6$ | $4.0 \cdot 10^6$ | 6.98 | 6.99 | 0.00% | 0.04 | 0.0% |
| $\varepsilon_T$ (Phantom) | | 80 | 60 | 6.98 | 7.40 | 0.30% | 2.00 | 0.6% |
| $\sigma$(Phantom) [S/m] | | 0.47 | 0.60 | 6.98 | 7.18 | 22.3% | 0.04 | 0.9% |
| Phantom Position X [mm] | $E_{RTS}$, incident | 0.0 | 10.0 | 300.9 | 302.2 | 0.04% | 1.15 | 0.1% |
| Phantom Position Y [mm] | [V/m] | 0.0 | 10.0 | 300.9 | 306.9 | 0.20% | 1.15 | 0.2% |

TABLE 1-continued

Uncertainty analysis. The methods used were based on the work of Neufeldet al.[42]. To evaluate the uncertainty of the quantities of interest derived by the simulations (i.e., 10 g-avg. SAR or the magnitude of incident electric field "$E_{RVS}$") Two simulations were run for each parameter by assigning two different values ("Val 1" and "Val 2") to each parameter studied. The first value ("Val 1") was the one used for the simulations shown in FIG. 2, whereas the modified value ("Val 2") was set to a realistic value that could occur due to either design choice or manufacturing tolerance. The results obtained for each value ("Result 1" and "Result 2", respectively) were used to evaluate sensitivity factor of the quantity evaluated (10 g-avg. SAR or magnitude of incident electric field "$E_{RVS}$"). The standard deviation ("Std. Dev.") was derived from literature

| Parameter | Quantity | Val 1 | Val 2 | Result 1 | Result 2 | Sensitivity factor [%/mm] | Std. Dev | Uncertainly [%] |
|---|---|---|---|---|---|---|---|---|
| Phantom Position Z [mm] | | 0.0 | 10.0 | 300.9 | 307.0 | 0.20% | 1.15 | 0.2% |
| Lead Position X [mm] | | 0.0 | 1.0 | 300.9 | 307.4 | 2.14% | 0.58 | 1.2% |
| Lead Position Y [mm] | | 0.0 | 1.0 | 300.9 | 299.2 | 0.57% | 0.58 | 0.3% |
| Lead Position Z [mm] | | 0.0 | 1.0 | 300.9 | 301.3 | 0.12% | 0.58 | 0.1% |

Manufacturing of Flat-Design RTS Prototype

Based on the optimal parameters of the RTS design's conductivity and length derived from simulations (see Table S1), a flat-design lead prototype was built using polymer thick-film (PTF) technology to experimentally test the proposed concept (see FIG. 3a). The lead was built by printing thin (10 mm) layers of two different commercially available conductive inks on a polymer substrate for the length of each of the two resistive layers. The dimensions of the RTS lead were chosen to obtain the same volume of the wire in the Medtronic 3389 lead (see Table S1 below).

TABLE S1

| Geometry | Dimension |
|---|---|
| Coil Diameter | 610 mm* |
| Coil Length | 620 mm* |
| Coil Shield Diameter | 660 mm* |
| Coil Shield Length | 1220 mm* |
| Coil and Shield Thickness | 0.1 mm* |
| Coil Ring/Rung Width | 25 mm* |
| Coil Former Inner Diameter | 590 mm* |
| Coil Former Wall Thickness | 10 mm* |
| Lead Length | 40 cm |
| Lead Width | 0.5 mm |
| Lead Thickness | 15.7 μm |
| Contact Length | 1.5 mm |
| Contact Width | 0.5 mm |
| Lead Substrate Width | 10 mm |
| Lead Substrate Thickness | 25 μm |
| Lead Insulation Width | 5 mm |
| Lead Insulation Thickness | 25 μm |

| Material | Value |
|---|---|
| Copper (Coil and Shield) Conductivity | 5.8 $10^7$ S/m |
| PMMA (Coil Former) Permittivity | 3.0 |
| Platinum (RTS Contact) Conductivity | 9.3 $10^6$ S/m |
| PtIr (Electrode/Wire) Conductivity | 4.0 · $10^6$ S/m |
| ASTM Phantom Conductivity | 0.47 S/m** |
| ASTM Phantom Permittivity | 80** |
| Kapton HN (Lead Substrate) Permittivity | 3.5 |
| DI-7502 (Lead Insulation) Permittivity | 2.5 |
| Conductive Ink (Lead) Permittivity | 5.0 |
| PAA Gel (ASTM Phantom) Thermal Diffusivity | 1.3 · $10^{-7}$ m/s²** |
| PAA Gel (ASTM Phantom) Specific Heat Capacity | 4150 J/(kg · C)** |
| PAA Gel (ASTM Phantom) Density | 1200 kg/m³** |

(Top) Dimension of numerical model. Coil dimensions (indicated with*) were based on the work of Yeo et al. [Ref. S29]
(Bottom) Electrical and thermal properties used for the simulations. The properties of the ASTM phantom (indicated with **) were based on the ASTM standard [Ref. S9].

Manufacturing of flat-design RTS prototype as shown at the bottom of in FIG. 1a. A flat-design RTS lead prototype was manufactured using two different commercially available conductive ink materials for initial proof-of-concept testing. The first ink (479SS, Electrodag, Acheson LTD., Kitano, Japan) is a silver (Ag) based PTF ink and was fixed to a specified resistivity of 0.02 Ω/sq./mil [Ref. S24]. This ink was used in the higher conductivity section $L_1$. The second ink (423, Electrodag) is a carbon (C) based PTF ink, which has significantly higher resistivity compared with Ag based PTF inks of 42 Ω/sq./mil [Ref. S25]. The final layer $L_2$ was fabricated by chemically mixing the two PTF inks to adjust the conductivity of the second section to the value prescribed by the simulations, which was constrained to be within the conductivity values of the Ag and C-based PTF inks. The length of layer 1 was proportional to the conductivity of the silver ink and was fixed to allow a target ratio $\sigma_1/\sigma_2=77$ with the optimal total resistance of 400Ω Notably, the resistivity of both the carbon traces and silver electrodes is constant from 100 Hz to 200 MHz [Ref. S21]. The 400Ω resistance was well within the range of current commercial IPGs considering that the contact electrode/tissue resistance is usually below 1.5 kΩ [Ref. S18]. The tolerance for resistivity was 5% and the tolerance for length was 50 μm.

Temperature Measurements in MRI

The RTS prototype was built by stacking four of the flat-design leads connected to four electrodes (see FIG. 3c) and by insulating the proximal end (opposite to the electrodes). The RTS prototype was then implanted in a standard ASTM phantom filled with a polyacrylic acid (PAA) mixed in an aqueous solution [Ref. 23] and tested in a 3 T MRI system (Skyra, Siemens, Erlangen, Germany) (see FIG. 3b). Three fiber optic temperature probes (Neoptix Inc., Quebec, Canada) were used to record the temperature in the phantom and along the lead under several conditions: no lead, RTS lead, and Medtronic 3389 lead (see FIG. 3d). RF energy was delivered to the phantom at First Level Controlled Operating Mode for 15 minutes.

Evaluation of RF-induced heating during MRI was assessed by loading the MRI RF body coil with a standard ASTM phantom 9 (FIG. 3b). The phantom shell was made of Plexiglas and filled to a volume of 24.6 L with a gel consisting of PAA (436364, Sigma Aldrich Co., St. Louis, Mo.), distilled water (conductivity less than $10^{-3}$ S/m), and reagent grade NaCl (S9888, Sigma Aldrich Co., St. Louis, Mo.). The ratio of the mixture was 1.32 g NaCl and 10 g PAA for each 1 L of water to obtain a conductivity of approximately 0.47 S/m at room temperature [Ref. S9]. The mixture created a semisolid gel that approximated the dielectric constant and thermal convection of human tissue [Ref. S26]. A plastic scaffold with adjustable posts (i.e., plastic screws, bolts and washers) was placed on the far right side of the phantom and was utilized to consistently position system components (i.e., electrode lead and temperature probes) within the phantom (FIGS. 3c and 3d). As shown in FIG. 1e, the electric field magnitude inside the phantom at 128 MHz in the selected configuration was highest in a location close to the body coil [Ref. S13]. In order to have high magnitude of electric field incident to the lead, the phantom was shifted as far right as possible within the bore and the leads were placed on the side of the phantom (FIG. 3b, FIGS. 1e and 1f). Temperature measurements were recorded using four fiber-optic temperature sensors compatible with MRI (Neoptix Reflex, Qualitrol LLC, Fairport, N.Y.). Three thermometry probes were positioned within the phantom to capture the temperature profiles of set points on the electrode lead. Probes were positioned (FIGS. 3c and 3d) perpendicular to the electrode contact (0.3 mm from the center of the contact), in-line with the tip (0.3 mm away from tip), and perpendicular to the middle of the lead (0.3 mm from center of lead)27. The 3 T MR system (Skyra, Siemens Medical Systems, Erlangen, Germany) used for imaging was programmed with parameters set to investigate high RF energy exposures that meet the maximum limit allowed for averaged SAR generated by an MRI scan (Turbo Spin-echo sequence, TR=654 ms; TE=16 ms; 180° flip angle; $1.2 \times 1.2 \times 1.2$ mm$^3$ voxel volume). Each experimental session consisted of a 5-minute epoch for baseline temperature recordings, a 15-minute MRI scan, and a 15-minute epoch post-scan to assess temperature decay rates. A commercially available DBS lead (3389, Medtronic Inc., Minneapolis, Minn.) and the RTS prototype were tested in the same sessions. The Medtronic 3389 lead was chosen because it is approved for use in MRI with very specific conditions [Ref. S28]. The proximal end of the Medtronic 3389 lead was not insulated. Temperature was recorded at 1-second intervals. A baseline experimental session in which no lead was positioned within the scaffolding of the phantom was conducted to establish the RF-induced heating of the phantom alone.

The design optimization was performed with a model of a body coil based on literature [Ref. S29]. In order to compare the temperature measurements with the simulations, additional simulations were performed with a second body coil model, matching the geometrical characteristics of the coil used in the MRI measurements (i.e., 70 cm diameter, 40 cm length, tuned to a Larmor frequency of 123.2 MHz). The coil was loaded with the ASTM phantom placed off-center, as in the experimental setup (FIG. 3b). FIG. 8 shows the results of the temperature simulations compared with the experimental measurements (shown also in FIG. 3e).

Implantable Pulse Generator (IPG) Battery Testing

Battery testing was also performed with both leads (flat-design RTS and Medtronic 3389) (see FIGS. 3f and 3g) connected to an IPG (i.e., Medtronic Activa® PC) through an extension. The IPG, extension, and lead were then placed in a quart of deionized water mixed with saline solution to simulate in-body tissue impedance. The IPG was turned on for a total of four weeks.

The testing was performed using the following parameter settings for the Activa PC IPG (Medtronic, Inc., Minneapolis, Minn.): (i) single lead (contact 0, according to the Medtronic numbering in FIG. 4d) set to negative (−), (ii) case set to positive (+ and contacts 1, 2 and 3 were all turned off), (iii) unipolar cathodic pulse train set to an amplitude of 2 V, a frequency of 130 Hz and a pulse width of 90 µs. For the Medtronic 3389 lead the following procedure was used: the extension wire was connected and fastened (with set screw) on one side to the IPG and on the other side to the lead. The connection site was covered with silicon wrap and sealed on both ends with non-dissolvable suture, which is the same procedure utilized in the operating room to produce a water tight implant. For the RTS lead the following procedure was used: the extension wire was connected and fastened (with set screw) to the IPG and the RTS lead was connected (contact 0) to the extension wire with silver epoxy (8331, MG Chemicals, Surrey B.C., Canada) and insulated with super glue. The connection site was covered with silicon wrap and sealed on both ends with non-dissolvable suture. A digital multimeter was used to check for conductivity between RTS contact and extension wire. For both leads, the IPG, extension, and lead were placed in a quart of deionized water. Saline solution at room temperature was added to the deionized water until the impedance measured 1500Ω. Because the lead impedance of the RTS prototype was higher than the Medtronic 3389 lead, a lower amount of saline solution was added for the latter case. A hand-held Medtronic Physician programmer was utilized to activate the IPG to test for therapeutic impedance. As the proprietary battery and circuit designs of the IPG were unknown, a direct quantification of power consumption could not be calculated. Therefore, battery level (in volts, analogous to the indicator on a cell phone or laptop) was measured using the handheld programmer. The battery level provides an indication of power consumption. Although the exact relationship between battery level and power consumption is not disclosed by the manufacturer, the changes in battery level recorded can still inform about possible changes in the amount of charge delivered when comparing the two lead designs. The IPG was turned on and left on for a total of four weeks; during this time the IPG was tested once a week by two measures, (1) an oscilloscope was used to check and measure the emitted pulse train in saline solution, and (2) the hand-held programmer was used to monitor changes in the therapeutic impedance. Saline was added to the water if impedance dropped below 1500Ω (FIGS. 4f and 4g). Testing was done with constant impedance to check that—with given conditions—the RTS would deliver the same charge compared to the Medtronic 3389. When implanted, the impedance of the RTS (~400Ω) would in fact be different from the Medtronic 3389 (~50Ω), which can result in a lower battery life or a shorter time period before recharging [Ref. S30]. However, any overall differences in total impedance would still be within the normal variability (between 500Ω and 1.5 kΩ) measured in patients a few weeks post-implantation [Ref. S18].

Manufacturing of Wire-Design RTS Prototype

A second RTS wire-design prototype was manufactured using thin-film physical vapor deposition (PVD) of titanium and gold over a rotating Ethilon® 6-0 nylon suture substrate, which was selected for its biocompatibility. Variation in the impedance of each segment is achieved by control of the thickness of the gold layer of each segment.

The second RTS wire prototype was manufactured using the state-of-the-art physical E-Beam physical vapor deposition (PVD) technology (Thin-Films Research, Inc., Westford, Mass.) over a rotating suture (Ethilon® 6-0, Ethicon Inc., Bridgewater, N.J.) substrate (80 µm diameter), which was selected for its biocompatibility. The polymer fiber core was composed of Ethilon® 6.0 (Ethicon Endo-Surgery Inc., Somerville, N.J.), a non-absorbable monofilament suture composed of the long-chain aliphatic polymers Nylon 6 and Nylon 6.6, due to its mechanical properties (e.g., tensile strength) and long history of use as a permanent implantable material [Ref. S31]. Ethilon® nylon has excellent mechanical properties, for instance the selected 6-0 fiber size or 80 µm has a maximum tensile strength of 6.68N [Ref. S32], which diminished by only 10% after thin film deposition. Ethilon® nylon has also a very high breaking stress of 6.25 GDP compared to other non-absorbable sutures [Ref. S33], which may increase long term mechanical stability and reduce likelihood of failures. The Ethilon® nylon core was coated first with titanium and then with gold, using PVD. The suture was first coated with a thin Ti layer (100 nanometers) to improve bonding between gold and the polymer core fiber [Ref. S32,S34]. Subsequently the two-layers of RTS microwire were formed by depositing gold layers of two different thicknesses, one for each layer (i.e., 600 nanometers for layer 1 and 1,000 nanometers for layer 2) to allow the creation of a different conductivity within each layer. The two thickness levels were selected in order for the two layers to match the conductivity prescribed by the simulations of FIG. 4. The gold coating produced the desired conductivity profiles while maintaining the proper resistivity and inductance properties. The RTS core was finally coated with Parylene (a polyp-xylylene) polymer) and marked with a biocompatible ink to indicate the direction in which the core is to be connected to the electrodes and the proximal connector. Parylene C was used for the conductor wire insulation since it can be applied at room temperature which avoids exposure of the RTS core wire to high temperatures during processing. Medical grade Parylene C is an excellent neural prosthetic coating as shown by the good encapsulation overall performance [Ref. S35]. The RTS wire will be inserted in the original Medtronic 3389 design, which has a stylet in the lumen which is removed during surgery that confers the implant the rigidity to reach the target. In regards to the long-term implantation, following the Medtronic 3389 design, the RTS wire will be completely encapsulated in biocompatible and implantable polymers that enhance durability.

Results

Electromagnetic simulations. The length of each individual section of the RTS lead affected the 10 g-avg. SAR near the electrode non-linearly (see FIG. 2a). Numerical simulations were repeated to observe the correlation between RTS design and 10 g-avg. SAR by fixing the length of each section and varying the ratio in conductivity ($\sigma_1$ and $\sigma_2$) between the two sections of the lead, while maintaining a total length of 40 centimeters. FIG. 2b shows the 10 g-avg. SAR in the phantom near the electrode with a resistance varying from 0Ω to 1 kΩ for several RTS designs. The RTS lead reduced the 10 g-avg. SAR across the entire range of resistances. The simulations showed an increase in conductivity ratio between the two sections that corresponded to a decrease in 10 g-avg. SAR at the electrode. For example, the optimal RTS (i.e., $\sigma_1/\sigma_2=200$) plateaued at 400Ω with a value of 4.02 W/kg, whereas the design with $\sigma_1/\sigma_2=2$ showed a 10 g-avg. SAR of 5.75 W/kg at 400Ω. For comparison, the peak 10 g-avg. SAR with a 40 cm PtIr wire was 222 W/kg. See FIG. 6 for additional maps of electric and magnetic field magnitude with RTS and PtIr wire.

The SAR reduction was due to a lower inductance of the RTS design (see FIG. 2c) (see also the "theoretical background on RTS design" above) that corresponded to a shorter equivalent antenna length and lower induced currents. Simulations with a single-section platinum-iridium (PtIr) wire of the same length (40 cm) were also performed for reference. As confirmed by the simulations, the RTS design was characterized by a reduced current at the electrode of over two orders of magnitude compared with the PtIr wire (see FIG. 2d). The high electrical conductivity of the ink used for manufacturing allowed a prototype to be built with the following characteristics: $\sigma_1=1.968\times10^6$ S/m, $\sigma_2=25.61\times10^3$ S/m (i.e., $\sigma_1/\sigma_2=76.86$), $L_1=0.367$ m, and $L_2=0.033$ m. The total resistance for the RTS design was chosen to be R=400Ω, five times less than the maximum electrode/tissue impedance of 2 kΩ allowed by even older IPG models [Ref. 40]. As shown in FIGS. 2a and 2b, the 10 g-avg. SAR of this configuration was expected to be very similar to the best performance of the RTS lead with ratio $\sigma_1/\sigma_2=200$ (i.e., 4.1 W/kg vs. 4.02 W/kg, respectively) (for discussion of the case $\sigma_1/\sigma_2=1$ as well as other additional cases, see FIG. 7).

Temperature simulations. FIG. 2 shows the 10 g-avg. SAR (see FIG. 2e) and temperature maps (see FIG. 2f) recorded in the phantom model under three conditions: without implant, with the RTS design selected for prototype manufacturing, and with the PtIr wire. The SAR and temperature maps, which are plotted throughout the plane containing the lead, show similar results between the phantom with the RTS lead vs. the phantom without implant. The peak 10 g-avg. SAR was less than 7 W/kg, and temperature changes were below 1° C. in both cases for a 15-minute exposure at a whole-body SAR of 2 W/kg. By contrast, the simulations with the PtIr wire model predicted a peak 10 g-avg. SAR of 230 W/kg and temperature change of 64° C. for the same exposure. As a reference, the value of 2 W/kg is the limit in Normal Operating Mode for SAR averaged over the entire body, as established by the current guidelines of the International Electrotechnical Commission (IEC) [Ref. 41].

Temperature measurements. The temperature increase near the electrode of the Medtronic 3389 lead was about 9° C. higher than the baseline level of the phantom without a lead and 2° C. near the middle of the lead. Conversely, the temperature increase of the RTS lead was 3° C. around the electrode and less than 4° C. near the middle of the lead (see FIG. 3e). These temperature values were consistent with the energy distributions predicted by the simulations (see FIG. 8) suggesting a decrease of current at the electrode and an increase of current along the lead. For comparison, the baseline temperature increase of the phantom without an implant was 1.5° C. at the location corresponding to the electrode and 1° C. at the location corresponding to the middle of the lead (see FIG. 3e). Given the linear relationship between SAR and temperature, the corresponding maximum temperature increases at 2 W/kg would be less than 4.5° C. with the Medtronic 3389 lead and less than 2° C. with the RTS. For reference, the level of temperature increase suggested by an international safety standard for patients with implantable neurostimulators is 2° C. [Ref. 43], which the RTS lead met in the experimental setup used in this Example.

Battery measurements. The longevity of the Activa PC Neurostimulator battery can last for months to years depending on the following factors: programmed stimulation parameters, the total system impedance and the hours per day the battery is in use. The Medtronic Battery Longevity Manual [Ref. 44] provides a formula that estimates the approximate period of time that an Activa PC battery can last. The formula utilizes the aforementioned factors to calculate an estimated energy use of the battery in a 24 hour period, which can then be used with a look-up chart (see FIG. 2 in Ref. 44) to predict battery longevity in years. For the battery testing conducted in this investigation, the programmed stimulation parameters, system impedance and hours per day of stimulation were fixed at the same values for both the RTS prototype and the Medtronic 3389 lead. Accordingly, longevity estimates for both leads will be the same. To assess whether actual battery consumption would correspond with such a prediction, a preliminary comparative test was performed by connecting the RTS prototype (see FIG. 3o and the Medtronic 3389 lead (see FIG. 3g) to the Activa PC Neurostimulator (Medtronic, Inc., Minneapolis, Minn.). Over a 30 day testing period, both leads showed only a 0.005 V drop in battery voltage, a result that correlates with Medtronic estimation methods. This indicates that the RTS design affects only the behavior of the lead with respect to RF (i.e., the reactance) and not with respect to the operational frequencies of the stimulator (see also the theoretical background on RTS design above).

DISCUSSION

This Example presents a novel metamaterial [Ref. 38] lead that reduces the antenna effect and allows for decreased tissue heating during MRI [Ref. 45]. The optimal parameters of the design were determined by computational modeling and simulations, validated against in-vitro temperature measurements in a gel-filled phantom (see FIG. 8). The numerical simulations confirmed that a PtIr wire acts as an antenna during the RF transmit period of the MRI scan, picking up the induced electric field and transferring a high amount of RF energy into the volume surrounding the exposed electrode tip. In both simulations and in-vitro testing the proposed RTS design successfully reduced the amount of energy absorbed and the related temperature increases inside the gel-phantom in proximity to the electrode. Numerical simulations and experimental testing confirmed that the RTS design allows for "RF-cloaking" [Ref. 38] while maintaining proper low-frequency conductivity that does not affect battery performance.

The experimental bench testing confirmed also the practical feasibility of the RTS design. The primary feature of the RTS is the abrupt change of conductivity between the two sections. While this discontinuity can be easily modeled computationally, issues can arise in a prototype, because the RTS needs to be built using different inks with different electrical properties. In practice, the two ink traces of the two different layers cannot be perfectly contiguous along the RTS; an overlap is always present which reduces the transition between the layers and, therefore, the ideal step discontinuity in electrical conductivity. The experimental testing confirmed that the prototype contained an adequate discontinuity between the two layers with a physical overlap between the two layers that was only about 50 mm along the RTS (see FIG. 5e). Additionally, the proposed RTS design does not require any external physical device such as an RF choke. RF chokes are difficult to attach to an implant wire because the dimensions of a choke are larger than the typical dimension of the wire. Chokes also disrupt the mechanical characteristics of an implant, which should be flexible [Ref. 46]. Although there are extremely miniaturized RF chokes, these devices can be more prone to burning because of the microscopic physical dimensions of their components.

In order to enhance the signal-to-noise ratio of the measurements, the testing was performed with high levels of RF power, namely one corresponding to a whole-body SAR of 4 W/kg as estimated by the MRI system. Most sequences used in MRI systems are characterized by a whole-body SAR of less than 2 W/kg. SAR estimation varies for each MRI manufacturer and across systems and depends on several variables, including coil specifications, landmarks, and patient registration information, e.g., weight, height, age. Ref 47 compared the RF-induced heating per unit of SAR due to the presence of a DBS lead between two 1.5 T MRI systems and observed values ranging from 3.5 to 5.5 times higher on one MRI system as compared to the other. As such, the absolute temperature values found in this study are specific to the MRI system used [Ref. 47]. Additionally, the measurements were performed in a gel-filled phantom [Ref. 12, 13, 31, 47]. This approach implies lack of perfusion and does not take into consideration possible changes due to the thermoregulatory response in a patient [Ref. 48]. Such a scenario is typically considered a worst-case, because perfusion can reduce significantly, e.g., two-fold, the heating of tissue in proximity of the lead [Ref. 49].

In this Example, heating in the proximity of DBS implants, induced by the RF excitation pulses during the MRI, was measured by fluoroptic temperature sensors, which are the "state-of-the-art" in this field [Ref. 31, 47, 50-53]. Another common approach for measuring temperature is MRI thermometry, which allows controlled heating while simultaneously measuring the spatial and temporal temperature distribution near the DBS implant. The most common MRI-thermometry method is based on proton resonance frequency shift (PRFS), which has been used to monitor temperature near a wire [Ref. 54]. However, the susceptibility artifact from the DBS implant may extend up to 5 mm from the electrode surface, and at this distance the temperature changes are significantly lower than the peak temperature change [Ref. 49]. Additional approaches were proposed to alleviate the susceptibility artifacts around a wire, but they did not provide real-time measurements at the desired high spatial resolution [Ref. 55,56], underestimating the peak temperature change. Conversely, fluoroptic thermometers can provide accurate and real time temperature measurements with a spatial resolution of typically 300 mm [Ref. 53].

The configuration of the implanted DBS components relative to the incident RF field and its orientation can also have a dramatic effect on the induced heating. In this Example, the lead orientation was limited to a single case of overall lead length and path within the phantom [Ref. 42], i.e., lead placed parallel to the magnet bore axis (see FIG. 1f). This allowed for the evaluation of the PtIr wire and the proposed RTS lead under the same conditions of high incident electric field (see FIG. 1e) inside the homogenous phantom used in the Example. However, the layout used does not necessarily model the exposure conditions of a lead implanted in a patient [Ref. 57], nor does it take into consideration differences between a single vs. bilateral lead. For example, a change in orientation of the lead with respect to a 1.5 T RF coil can generate changes in temperature of 20° C. or more in a phantom [Ref. 58]. A full systematic analysis of safety of the proposed RTS lead is still required and would need to include several configurations that would mimic clinically significant pathways, in line with the technical specifications proposed for safety analysis of patients with active implanted devices undergoing MRI [Ref. 12,59]. Additional numerical simulations were performed with an electrically heterogeneous, anatomically precise human head and torso model [Ref. 60,61] containing a DBS lead reproducing a clinical case (see FIG. 4b)—as shown by CT imaging (see FIG. 4a)—for testing under different exposure and geometrical conditions. The model was placed with the head in the isocenter of an MRI coil (see FIG. 4c). FIGS. 4f and 4g show a coronal and sagittal view the SAR in the head and body without an implanted lead, with a lead made of platinum iridium wire, and with an optimized wire-design RTS lead. These results also confirmed the advantage of the RTS design which significantly reduces absorbed power in the brain parenchymal near the electrode.

The benefits of the electrically thin design with its scattering behavior (see theoretical background on RTS design above) can be used to replace any wire currently used in commercially available implant leads by coating a suture with biocompatible metals. Hence, a second more realistic and biocompatible RTS wire prototype was created (see FIG. 5a). Optical microscope (OM) images show the raw suture (see FIG. 5b) before thin film deposition and after deposition (see FIG. 5d). The abrupt transition of electrical conductivity between the two RTS layers (see FIG. 5c) maximizes the mismatched impedance and the scattering within the fibers (see FIG. 1 and theoretical background on RTS design above). The two different layers of the RTS fiber and the surface characteristics were also studied with a scanning electron microscope (SEM) (see FIG. 5e and FIG. 5f) in order to better characterize the transition between the two layers.

The final RTS lead configuration is assembled similarly to the configuration of the Medtronic 3389 DBS lead (see FIG. 4d) and thus it may be used (i.e., interchangeable) with the Medtronic Activa stimulator. Each lead comprises an implantable grade polyurethane inner shaft, into which the stylet is advanced, that terminates at the hermetically sealed distal tip of the lead. The RTS fibers are positioned around the inner shaft and contained within a protective sheath that has four platinum/iridium electrodes near the tip for delivery of stimulation to the target site. The proximal end of the lead also has four electrodes that interface with the implanted stimulation device after implantation. The leads are stereotactically introduced into the target and fixed at the skull with a burr hole cap and ring, as for the Medtronic DBS leads.

CONCLUSION

This Example presents a novel resistive-tapered stripline (RTS) lead design that "cloaks" the radiofrequency fields induced by magnetic resonance imaging (MRI) to reduce tissue heating, yet maintains the conduction of low-frequency stimulation from implanted medical devices. Computational modeling and simulations were used to find the optimal design parameters of the RTS lead. Polymer thick-film (PTF) technology was used to manufacture an initial prototype, which was tested in a 3 T MRI system showing a significant reduction of heating when compared to a Medtronic 3389 lead. Finally, state-of-the-art physical vapor deposition (PVD) technology was used to manufacture a biocompatible RTS wire prototype, which may easily replace any wire currently used in commercially available implant leads. The results show the proposed design may allow a significant increase in the number of patients with medical implants having safe access to the diagnostic benefits of magnetic resonance imaging.

REFERENCES

1. D'Haese, P. F. et al. Clinical accuracy of a customized stereotactic platform for deep brain stimulation after accounting for brain shift. Stereotactic and functional neurosurgery 88, 81-87, doi:10.1159/000271823 (2010).
2. Arantes, P. R. et al. Performing functional magnetic resonance imaging in patients with Parkinson's disease treated with deep brain stimulation. Movement disorders: official journal of the Movement Disorder Society 21, 1154-1162 (2006).
3. Fleming, S. M., Thomas, C. L. & Dolan, R. J. Overcoming status quo bias in the human brain. Proceedings of the National Academy of Sciences of the United States of America 107, 6005-6009, doi:10.1073/pnas.0910380107 (2010).
4. Shellock, F. G. & Spinazzi, A. MRI safety update 2008: part 2, screening patients for MRI. AJR. American journal of roentgenology 191, 1140-1149, doi:10.2214/AJR.08.1038.2 (2008).
5. Guy, A. Biophysics-energy absorption and distribution. AGARD Lecture Series, Radiation Hazards (Non-ionizing Radiations—Biological Effects and Safety Considerations 78 (1975).
6. Buchli, R., Boesiger, P. & Meier, D. Heating effects of metallic implants by MRI examinations. Magnetic resonance in medicine: official journal of the Society of Magnetic Resonance in Medicine/Society of Magnetic Resonance in Medicine 7, 255-261 (1988).
7. Chou, C. K., McDougall, J. A. & Chan, K. W. RF heating of implanted spinal fusion stimulator during magnetic resonance imaging. IEEE transactions on bio-medical engineering 44, 367-373, doi:10.1109/10.568912 (1997).
8. Angelone, L. M. et al. Metallic electrodes and leads in simultaneous EEG-MRI: specific absorption rate (SAR) simulation studies. Bioelectromagnetics 25, 285-295, doi: 10.1002/bem.10198 (2004).
9. Angelone, L. M., Ahveninen, J., Belliveau, J. W. & Bonmassar, G. Analysis of the role of lead resistivity in specific absorption rate for deep brain stimulator leads at 3 T MRI. IEEE transactions on medical imaging 29, 1029-1038, doi:10.1109/TMI.2010.2040624 (2010).
10. Angelone, L. M., Bit-Babik, G. & Chou, C. K. Computational electromagnetic analysis in a human head model with EEG electrodes and leads exposed to RF-field sources at 915 MHz and 1748 MHz. Radiation research 174, 91-100, doi:10.1667/RR1933.1 (2010).
11. Bassen, H., Kainz, W., Mendoza, G. & Kellom, T. MRI-induced heating of selected thin wire metallic implants—laboratory and computational studies—findings and new questions raised. Minimally invasive therapy & allied technologies: MITAT: official journal of the Society for Minimally Invasive Therapy 15, 76-84, doi:10.1080/13645700600640931 (2006).
12. Cabot, E. et al. Evaluation of the RF heating of a generic deep brain stimulator exposed in 1.5 T magnetic resonance scanners. Bioelectromagnetics 34, 104-113, doi: 10.1002/bem.21745 (2013).
13. Rezai, A. R. et al. Neurostimulation systems for deep brain stimulation: in vitro evaluation of magnetic resonance imaging-related heating at 1.5 tesla. Journal of magnetic resonance imaging: JMRI 15, 241-250 (2002).
14. Shrivastava, D. et al. Effect of the extracranial deep brain stimulation lead on radiofrequency heating at 9.4 Tesla (400.2 MHz). Journal of magnetic resonance imaging: JMRI 32, 600-607, doi:10.1002/jmri.22292 (2010).
15. Spiegel, J. et al. Transient dystonia following magnetic resonance imaging in a patient with deep brain stimulation electrodes for the treatment of Parkinson disease. Case report. Journal of neurosurgery 99, 772-774 (2003).
16. Henderson, J. M. et al. Permanent neurological deficit related to magnetic resonance imaging in a patient with implanted deep brain stimulation electrodes for Parkinson's disease: case report. Neurosurgery 57, E1063 (2005).

17. ASTM-F2503-13. International Standard Practice for Marking Medical Devices and Other Items for Safety in the Magnetic Resonance Environment, http://www.astm.org/Standards/F2503.htm. (2013—Date of access: 27 Jan. 2015).
18. Chhabra, V. et al. Safety of magnetic resonance imaging of deep brain stimulator systems: a serial imaging and clinical retrospective study. Journal of neurosurgery 112, 497-502, doi:10.3171/2009.7.JNS09572 (2010).
19. Medtronic. Reference Manual—MRI guidelines for Medtronic Deep Brain Stimulation Systems., http://professional.medtronic.com/pt/neuro/dbs-md/ind/mri-guidelines/#.VKwRYnsz_qQ. (2010—Date of access: 27 Jan. 2015).
20. Dormont, D. et al. Neuroimaging and deep brain stimulation. AJNR. American journal of neuroradiology 31, 15-23, doi:10.3174/ajnr.A1644 (2010).
21. Mullinger, K. J., Mayhew, S. D., Bagshaw, A. P., Bowtell, R. & Francis, S. T. Poststimulus undershoots in cerebral blood flow and BOLD fMRI responses are modulated by poststimulus neuronal activity. Proceedings of the National Academy of Sciences of the United States of America 110, 13636-13641, doi:10.1073/pnas.1221287110 (2013).
22. Kundu, P. et al. Integrated strategy for improving functional connectivity mapping using multiecho fMRI. Proceedings of the National Academy of Sciences of the United States of America 110, 16187-16192, doi:10.1073/pnas.1301725110 (2013).
23. ASTM-F2182-11. Standard Test Method for Measurement of Radio Frequency Induced Heating On or Near Passive Implants During Magnetic Resonance Imaging, http://www.astm.org/Standards/F2182.htm. (2011—Date of access: 27 Jan. 2015)
24. Ladd, M. E. & Quick, H. H. Reduction of resonant RF heating in intravascular catheters using coaxial chokes. Magnetic resonance in medicine: official journal of the Society of Magnetic Resonance in Medicine/Society of Magnetic Resonance in Medicine 43, 615-619 (2000).
25. Chou, C. K. & Guy, A. W. Carbon-loaded Teflon electrodes for chronic EEG recordings in microwave research. The Journal of microwave power 14, 399-404 (1979).
26. Bonmassar, G., Hadjikhani, N., Ives, J. R., Hinton, D. & Belliveau, J. W. Influence of EEG electrodes on the BOLD fMRI signal. Human brain mapping 14, 108-115 (2001).
27. Lemieux, L. et al. Event-related fMRI with simultaneous and continuous EEG: description of the method and initial case report. NeuroImage 14, 780-787, doi:10.1006/nimg.2001.0853 (2001).
28. Goldman, R. I., Stern, J. M., Engel, J., Jr. & Cohen, M. S. Acquiring simultaneous EEG and functional MRI. Clinical neurophysiology: official journal of the International Federation of Clinical Neurophysiology 111, 1974-1980 (2000).
29. Chou, C. K. Electromagnetic Fields, Bioeffects Research, Medical Applications, and Standards Harmonization International EMF Conference (ed N D Montgomery K H Ng, and L K Tan), 37-40. (2007).
30. Maged, M. E., Abhishek, D., Asif, R. & Marom, B. Temperature control at DBS electrodes using a heat sink: experimentally validated FEM model of DBS lead architecture. J Neural Eng 9, 046009 (2012).
31. Gray, R. W., Bibens, W. T. & Shellock, F. G. Simple design changes to wires to substantially reduce MRI-induced heating at 1.5 T: implications for implanted leads. Magnetic resonance imaging 23, 887-891, doi:10.1016/j.mri.2005.07.005 (2005).
32. Bonmassar, G. Resistive Tapered Stripline (RTS) in Electroencephalogram Recordings During MRI. IEEE Trans on Microw Theory and Tech 52, 1992-1998 (2004).
33. Harlow, E. H. Why breakwaters break. OCEANS '88 Proceedings. 'A Partnership of Marine Interests', 1250-1252 (1988).
34. Peng, S. Rigorous formulation of scattering and guidance by dielectric grating waveguide: general case of oblique incidence. J. Opt. Soc. Am. A 6, 1869-1883 (1989).
35. Gaylord, T. & Moharam, M. Analysis and applications of optical diffraction by gratings. Proc. IEEE 73, 894-937 (1985).
36. Yang, L. & Xu, S. Multimode network analysis of dielectric periodic structures by an oblique incidence. Int J of Infrared and Millimeter Waves 21, 1807-1823 (2000).
37. Harmuth, H. On the Effect of Absorbing Materials on Electromagnetic Waves with Large Relative Bandwidth. IEEE Trans Electromag Compat 25, 32-39 (1983).
38. Schurig, D. et al. Metamaterial electromagnetic cloak at microwave frequencies. Science 314, 977-980, doi: 10.1126/science.1133628 (2006).
39. Yeo, D. T., Wang, Z., Loew, W., Vogel, M. W. & Hancu, I. Local specific absorption rate in high-pass birdcage and transverse electromagnetic body coils for multiple human body models in clinical landmark positions at 3 T. Journal of magnetic resonance imaging: JMRI 33, 1209-1217, doi:10.1002/jmri.22544 (2011).
40. Volkmann, J., Herzog, J., Kopper, F. & Deuschl, G. Introduction to the programming of deep brain stimulators. Movement disorders: official journal of the Movement Disorder Society 17 Suppl 3, S181-187 (2002).
41. IEC-60601-2-33. International Electrotechnical Commission—International Standard, medical equipment—part 2-33: Particular requirements for the safety of the magnetic resonance equipment for medical diagnosis, 3rd edition, 2010).
42. Neufeld, E., Kuhn, S., Szekely, G. & Kuster, N. Measurement, simulation and uncertainty assessment of implant heating during MRI. Physics in medicine and biology 54, 4151-4169, doi:10.1088/0031-9155/54/13/012 (2009).
43. ANSI-AAMI-ISO-14708. International Standard: Implants for surgery—Active implantable medical devices—Part 1: General requirements for safety, marking and for information to be provided by the manufacturer, https://www.iso.org/obp/ui/#iso:std:iso:14708:-1:ed-2:v1:en. (2014—Date of access: 27 Jan. 2015)
44. Medtronic. Reference Manual—System Eligibility Battery Longevity—Neurostimulation systems for deep brain stimulation, http://manuals.medtronic.com/wcm/groups/mdtcom_sg/@emanuals/@era/neuro/documents/documents/contrib_205868.pdf. (2014—Date of access: 7 Apr. 2015).
45. Bonmassar, G. & Eskandar, E. N. (Inventors and Assignee). MRI compatible leads for a deep brain stimulation system, U.S. patent application US20140249612 A1 (2014).
46. Bonmassar, G., Fujimoto, K. & Golby, A. J. PTFOS: flexible and absorbable intracranial electrodes for magnetic resonance imaging. PLoS one 7 doi:10.1371/journal.pone.0041187 (2012).
47. Baker, K. B., Tkach, J. A., Phillips, M. D. & Rezai, A. R. Variability in RF-induced heating of a deep brain stimulation implant across MR systems. Journal of magnetic resonance imaging: JMRI 24, 1236-1242, doi: 10.1002/jmri.20769 (2006).
48. Adair, E. R. & Black, D. R. Thermoregulatory responses to RF energy absorption. Bioelectromagnetics Suppl 6, S17-38, doi:10.1002/bem.10133 (2003).
49. Shrivastava, D. et al. Heating induced near deep brain stimulation lead electrodes during magnetic resonance imaging with a 3 T transceive volume head coil. Physics in medicine and biology 57, 5651-5665, doi: 10.1088/0031-9155/57/17/5651 (2012).
50. Sharan, A. et al. MR safety in patients with implanted deep brain stimulation systems (DBS). Acta neurochirurgica. Supplement 87, 141-145 (2003).
51. Baker, K. B. et al. Evaluation of specific absorption rate as a dosimeter of MRI-related implant heating. Journal of magnetic resonance imaging: JMRI 20, 315-320, doi: 10.1002/jmri.20103 (2004).
52. Bhidayasiri, R. et al. Bilateral neurostimulation systems used for deep brain stimulation: in vitro study of MRI-related heating at 1.5 T and implications for clinical imaging of the brain. Magnetic resonance imaging 23, 549-555, doi:10.1016/j.mri.2005.02.007 (2005).
53. Mattei, E. et al. Temperature and SAR measurement errors in the evaluation of metallic linear structures heating during MRI using fluoroptic probes. Physics in medicine and biology 52, 1633-1646 (2007).
54. Ehses, P. et al. MRI thermometry: Fast mapping of RF-induced heating along conductive wires. Magnetic resonance in medicine: official journal of the Society of Magnetic Resonance in Medicine/Society of Magnetic Resonance in Medicine 60, 457-461, doi:10.1002/mrm.21417 (2008).
55. Detti, V., Grenier, D., Perrin, E. & Beuf, O. Assessment of radiofrequency self-heating around a metallic wire with MR T1-based thermometry. Magnetic resonance in medicine: official journal of the Society of Magnetic Resonance in Medicine/Society of Magnetic Resonance in Medicine 66, 448-455, doi:10.1002/mrm.22834 (2011).
56. Gensler, D. et al. MR safety: fast T(1) thermometry of the RF-induced heating of medical devices. Magnetic resonance in medicine: official journal of the Society of Magnetic Resonance in Medicine/Society of Magnetic Resonance in Medicine 68, 1593-1599, doi:10.1002/mrm.24171 (2012).
57. Fraix, V. et al. Effects of magnetic resonance imaging in patients with implanted deep brain stimulation systems. Journal of neurosurgery 113, 1242-1245, doi:10.3171/2010.1.JNS09951 (2010).
58. Mattei, E. et al. Complexity of MRI induced heating on metallic leads: experimental measurements of 374 configurations. Biomedical engineering online 7, 11, doi: 10.1186/1475-925X-7-11 (2008).
59. ISO/TS-10974. Technical Specifications—Assessment of the safety of magnetic resonance imaging for patients with an active implantable medical device. (2012).
60. Makris, N. et al. MRI-based anatomical model of the human head for specific absorption rate mapping. Medical & biological engineering & computing 46, 1239-1251, doi:10.1007/s11517-008-0414-z (2008).
61. Massire, A. et al. Thermal simulations in the human head for high field MRI using parallel transmission. Journal of magnetic resonance imaging: JMRI 35, 1312-1321, doi: 10.1002/jmri.23542 (2012).

S1. Kanda, M. A relatively short cylindrical broadband antenna with tapered resistive loading for picosecond pulse measurements. *IEEE Trans Antennas Propag* AP-26 (1978).
S2. Wu, T. T. & King, R. The cylindrical antenna with nonreflecting resistive loading. *IEEE Trans Antennas Propag* AP-13, 369-373 (1965).
S3. Taflove, A. & Hagness, S. C. *Computational electrodynamics: the finite-difference time-domain method.* 2nd/edn, (Artech House, 2000).
S4. Bonmassar, G. Resistive Tapered Stripline (RTS) in Electroencephalogram Recordings During MRI. *IEEE Trans on Microw Theory and Tech* 52, 1992-1998 (2004).
S5. Jin, J.-M. *The finite element method in electromagnetics.* (Wiley, 1993).
S6. Orfanidis, J. *Electromagnetic Waves and Antennas*, www.ece.rutgers.edu/~orfanidi/ewa. (2013).
S7. Levy, M. *Parabolic equation methods for electromagnetic wave propagation.* (Institution of Electrical Engineers, 2000).
S8. Bassen, H., Kainz, W., Mendoza, G. & Kellom, T. MRI-induced heating of selected thin wire metallic implants—laboratory and computational studies—findings and new questions raised. *Minimally invasive therapy & allied technologies: MITAT: official journal of the Society for Minimally Invasive Therapy* 15, 76-84, doi:10.1080/13645700600640931 (2006).
S9. ASTM-F2182-11. *Standard Test Method for Measurement of Radio Frequency Induced Heating On or Near Passive Implants During Magnetic Resonance Imaging*, <http://www.astm.org/Standards/F2182.htm>(2011—Date of access: 27 Jan. 2015).
S10. Bonmassar, G., Serano, P. & Angelone, L. M. Specific absorption rate in a standard phantom containing a Deep Brain Stimulation lead at 3 Tesla MRI. *6th International IEEE/EMBS Conference on Neural Engineering (NER)*, 747-750, doi:10.1109/ner.2013.6696042 (2013).
S11. Kozlov, M. & Turner, R. Fast MRI coil analysis based on 3-D electromagnetic and RF circuit co-simulation. *Journal of magnetic resonance* 200, 147-152, doi: 10.1016/j.jmr.2009.06.005 (2009).
S12. Guy, A. Biophysics-energy absorption and distribution. *AGARD Lecture Series, Radiation Hazards (Non-ionizing Radiations—Biological Effects and Safety Considerations* 78 (1975).
S13. Neufeld, E., Kuhn, S., Szekely, G. & Kuster, N. Measurement, simulation and uncertainty assessment of implant heating during MRI. *Physics in medicine and biology* 54, 4151-4169, doi:10.1088/0031-9155/54/13/012 (2009).
S14. Mohsin, S. A., Sheikh, N. M. & Saeed, U. MRI-induced heating of deep brain stimulation leads. *Physics in medicine and biology* 53, 5745-5756, doi:10.1088/0031-9155/53/20/012 (2008).
S15. IEC-60601-2-33. *International Electrotechnical Commission-International Standard, medical equipment-part 2-33: Particular requirements for the safety of the magnetic resonance equipment for medical diagnosis,* 3rd edition, 2010).
S16. Jin, J.-M. *Electromagnetic analysis and design in magnetic resonance imaging.* (CRC Press, 1999).
S17. Rezai, A. R. et al. Neurostimulation systems for deep brain stimulation: in vitro evaluation of magnetic resonance imaging-related heating at 1.5 tesla. *Journal of magnetic resonance imaging: JMRI* 15, 241-250 (2002).
S18. Volkmann, J., Herzog, J., Kopper, F. & Deuschl, G. Introduction to the programming of deep brain stimulators. *Movement disorders: official journal of the Movement Disorder Society* 17 Suppl 3, S181-187 (2002).

S19. Merilampi, S. L. et al. The Effect of Conductive Ink Layer Thickness on the Functioning of Printed UHF RFID Antennas. *Proceedings of the IEEE* 98, 1610-1619, doi:10.1109/jproc.2010.2050570 (2010).

S20. Osborne, I., Lavine, M. & Coontz, R. Materials for electronics. Looking beyond silicon. Introduction. *Science* 327, 1595, doi:10.1126/science.327.5973.1595 (2010).

S21. Bonmassar, G., Fujimoto, K. & Golby, A. J. PTFOS: flexible and absorbable intracranial electrodes for magnetic resonance imaging. *PloS one* 7, doi:10.1371/journal.pone.0041187 (2012).

S22. Blythe, A. R. & Bloor, D. *Electrical properties of polymers*. 2nd edn, (Cambridge University Press, 2005).

S23. Dang, Z. M., Wang, L., Yin, Y., Zhang, Q. & Lei, Q. Q. Giant Dielectric Permittivities in Functionalized Carbon-Nanotube/Electroactive-Polymer Nanocomposites. *Adv Mater* 19, 852-857, doi:10.1002/adma.200600703 (2007).

S24. Acheson. Product Data Sheet Electrodag 423SS Graphite Based Polymer Thick Film Ink. (2005).

S25. Acheson. Technical Datasheet Electrodag 479SS 2(2010).

S26. Kato, H. et al. Composition of MRI phantom equivalent to human tissues. *Medical physics* 32, 3199-3208 (2005).

S27. Mattei, E. et al. Temperature and SAR measurement errors in the evaluation of metallic linear structures heating during MRI using fluoroptic probes. *Physics in medicine and biology* 52, 1633-1646 (2007).

S28. Medtronic. *Reference Manual-MRI guidelines for Medtronic Deep Brain Stimulation Systems*., <http://professional.medtronic.com/pt/neuro/dbs-md/ind/mri-guidelines/#.VKwRYnsz_qQ>(2010—Date of access: 27 Jan. 2015).

S29. Yeo, D. T., Wang, Z., Loew, W., Vogel, M. W. & Hancu, I. Local specific absorption rate in high-pass birdcage and transverse electromagnetic body coils for multiple human body models in clinical landmark positions at 3 T. *Journal of magnetic resonance imaging: JMRI* 33, 1209-1217, doi:10.1002/jmri.22544 (2011).

S30. Medtronic. *Reference Manual-System Eligibility Battery Longevity-Neurostimulation systems for deep brain stimulation*, http://manuals.medtronic.com/wcm/groups/mdtcom_sg/@emanuals/@era/@neuro/documents/documents/wcm_prod067815.pdf> (2010—Date of access: 27 Jan. 2015).

S31. Toda, H. et al. A novel composite targeting method using high-field magnetic resonance imaging for subthalamic nucleus deep brain stimulation. *Journal of neurosurgery* 111, 737-745, doi:10.3171/2008.12.JNS0861 (2009).

S32. Ratner, B. D., Tyler, B. J. & Chilkoti, A. Analysis of biomedical polymer surfaces: polyurethanes and plasma-deposited thin films. *Clinical materials* 13, 71-84 (1993).

S33. Chu, C. C. Mechanical properties of suture materials: an important characterization. *Annals of surgery* 193, 365-371 (1981).

S34. Gonzalez, C. & Rodriguez, M. A flexible perforated microelectrode array probe for action potential recording in nerve and muscle tissues. *Journal of neuroscience methods* 72, 189-195 (1997).

S35. Hassler, C., von Metzen, R. P., Ruther, P. & Stieglitz, T. Characterization of parylene C as an encapsulation material for implanted neural prostheses. *Journal of biomedical materials research. Part B, Applied biomaterials* 93, 266-274, doi:10.1002/jbm.b.31584 (2010).

S36. Collins, C. M. & Smith, M. B. Signal-to-noise ratio and absorbed power as functions of main magnetic field strength, and definition of "90 degrees" RF pulse for the head in the birdcage coil. *Magnetic resonance in medicine: official journal of the Society of Magnetic Resonance in Medicine/Society of Magnetic Resonance in Medicine* 45, 684-691 (2001).

The citation of any document is not to be construed as an admission that it is prior art with respect to the present invention.

Thus, the invention provides a lead for an implanted medical device in which the lead is adapted for electrical communication with an electrical signal source and has a distal tip with an electrode. The lead comprises a wire adapted to be placed in electrical communication with electrode. The wire includes: (i) a core comprising a polymeric material, and (ii) a metallic layer surrounding an outer surface of the core. The metallic layer includes a first section having a first thickness and a second section having a second thickness, wherein the first thickness is greater than the second thickness. The lead is substantially transparent to radio frequency waves in clinically-applicable magnetic resonance environments to reduce radio frequency absorption and avoid substantial heating effects.

Although the present invention has been described in detail with reference to certain embodiments, one skilled in the art will appreciate that the present invention can be practiced by other than the described embodiments, which have been presented for purposes of illustration and not of limitation. Therefore, the scope of the appended claims should not be limited to the embodiments contained herein.

What is claimed is:

1. A lead for an implanted medical device in which the lead is adapted for electrical communication with an electrical signal source and has a distal tip with an electrode, the lead comprising:

a wire adapted to be placed in electrical communication with the electrode, the wire including (i) a core comprising a polymeric material, (ii) a continuous metallic layer surrounding and contacting an outer surface of the core, the continuous metallic layer extending along the core a first length and having a layer thickness, and (iii) an outer metallic layer disposed on the continuous metallic layer, the outer metallic layer extending axially along the first length and having a first section and a second section, the first section defined by a first thickness greater than the layer thickness, the first section extending continuously and axially along the continuous metallic layer toward the second section, the second section having a second thickness greater than the first thickness and extending continuously and axially away from the first section, the first section having a first resistance and the second section having a second resistance different than the first resistance, wherein the lead is substantially transparent to radio frequency waves in clinically-applicable magnetic resonance environments to reduce radio frequency absorption and avoid substantial heating effects.

2. The lead of claim 1 wherein:

the continuous metallic layer comprises a metallic material selected from the group consisting of gold, titanium, platinum, cobalt-chromium alloys, cobalt, stainless steel, and mixtures thereof.

3. The lead of claim 1 wherein:
the first section of the outer metallic layer comprises a metallic material selected from the group consisting of gold, titanium, platinum, cobalt-chromium alloys, cobalt, and stainless steel, and the second section of the outer metallic layer comprises a metallic material selected from the group consisting of gold, titanium, platinum, cobalt-chromium alloys, cobalt, and stainless steel.

4. The lead of claim 3 wherein:
a thickness of the continuous metallic layer is in a range of 50 to 500 nanometers,
the second thickness is in a range of 200 to 1500 nanometers,
the first thickness is in a range of 100 to 1000 nanometers, and
the core is cylindrical and has a diameter in a range of 10 to 500 microns.

5. The lead of claim 1 wherein:
the polymeric material is selected from the group consisting of nylons, polyesters, polyolefins, fluoropolymers, polyurethanes, and polyaryletherketones.

6. The lead of claim 1 further comprising:
a terminal located at the distal tip of the wire.

7. The lead of claim 6 wherein:
the terminal has a tapered inner or outer surface.

8. An implantable medical device comprising:
the electrical signal source; and
the lead of claim 1,
wherein the wire places the electrical signal source and the electrode in electrical communication with one another, and
wherein the implantable medical device is selected from deep brain stimulation systems, cardioverter defibrillators, pacemakers, and spinal cord stimulators.

9. The implantable medical device of claim 8 wherein:
the implantable medical device is a deep brain stimulation system.

10. A lead for an implanted medical device in which the lead is adapted for electrical communication with an electrical signal source and has a distal tip with an electrode, the lead comprising:
a wire adapted to be placed in electrical communication with the electrode, the wire including (i) a core comprising a polymeric material, and (ii) a metallic layer surrounding an outer surface of the core, the metallic layer including an inner metallic layer bonded to the core and an outer metallic layer bonded to the inner metallic layer, the inner metallic layer and the outer metallic layer extending along an axial length of the wire, and wherein the outer metallic layer includes a first section and a second section, the first section formed at a first end of the wire and extending axially to the second section formed at a second end of the wire opposite the first end, the first section having a first thickness and a first axial length less than the axial length of the wire and the second section having a second thickness differing from the first thickness and a second axial length less than the axial length of the wire and differing from the first axial length, the first section and second section having different resistances to form a step discontinuity in electrical conductivity along the axial length of the wire,
wherein the lead is substantially transparent to radio frequency waves in clinically-applicable magnetic resonance environments to reduce radio frequency absorption and avoid substantial heating effects.

11. The lead of claim 10 wherein:
the polymeric material is selected from the group consisting of nylons, polyesters, polyolefins, fluoropolymers, polyurethanes, and polyaryletherketones, and
the metallic layer comprises a metallic material selected from the group consisting of gold, titanium, platinum, cobalt-chromium alloys, cobalt, and stainless steel, and mixtures thereof.

12. The lead of claim 11 wherein:
the first thickness is in a range of 200 to 2000 nanometers,
the second thickness is in a range of 100 to 1900 nanometers, and
the core is cylindrical and has a diameter in a range of 10 to 500 microns.

13. The lead of claim 10 further comprising:
a terminal located at the distal tip of the wire, the terminal having a tapered inner or outer surface.

14. The lead of claim 10 wherein:
the lead is configured such that it does not heat more than 2 degrees Celsius when placed within a magnetic resonance imaging device supplying an applied field of 3 Tesla.

15. The lead of claim 10 further comprising:
an insulating outer coating on the wire.

16. An implantable medical device comprising:
the electrical signal source; and
the lead of claim 10,
wherein the implantable medical device is a deep brain stimulation system.

* * * * *

UNITED STATES PATENT AND TRADEMARK OFFICE
CERTIFICATE OF CORRECTION

PATENT NO. : 10,335,590 B2  
APPLICATION NO. : 14/850229  
DATED : July 2, 2019  
INVENTOR(S) : Husman Katnani et al.

Page 1 of 1

It is certified that error appears in the above-identified patent and that said Letters Patent is hereby corrected as shown below:

In the Specification

Column 3, Line 52, "Figure if" should be --FIG. 1f--.

Column 9, Line 35, "polyp-xylylene)" should be --poly(p-xylyene)--.

Column 14, Line 46, Eq. (S3), "$0>\sigma_1+\sigma_2+\sigma_T \cdot L_1+L_2=L$" should be --$0>\sigma_1+\sigma_2+\sigma_T$ , $L_1+L_2=L$--.

Column 14, Line 58, Eq. (S4), "$L_{max} = \mu \dfrac{\iiint_x \|H(x,y,z)\|^2 dxdydz}{\left(\iint_{\delta_{1,2}} J(x,y,z \cdot k(x,y,z) ds\right)^2}$"

should be -- $L_{max} = \mu \dfrac{\iiint_x \|H(x,y,z)\|^2 dxdydz}{\left(\iint_{\theta_{1,2}} J(x,y,z \cdot k(x,y,z) ds\right)^2}$ --.

Column 15, Line 45, Eq. (S7), "$G(z-z') = \dfrac{e^{-jkR}}{R} \cdot R\sqrt{(z-z')^2 + \dfrac{d^2}{4}}$"

should be -- $G(z-z') = \dfrac{e^{-jkR}}{R}, \; R\sqrt{(z-z')^2 + \dfrac{d^2}{4}}$ --.

Column 25, Line 23, "(a polyp-xylylene)" should be --(a poly(p-xylylene)--.

Signed and Sealed this  
Third Day of September, 2019

Andrei Iancu  
*Director of the United States Patent and Trademark Office*